(12) United States Patent
Arnold et al.

(10) Patent No.: US 11,737,758 B2
(45) Date of Patent: Aug. 29, 2023

(54) COMPRESSION AND FIRING FORCE SENSOR FOR CIRCULAR SURGICAL STAPLER

(71) Applicant: Cilag GmbH International, Zug (CH)

(72) Inventors: Bradley A. Arnold, Mason, OH (US); Logan R. Rose, Loveland, OH (US)

(73) Assignee: Cilag GmbH International, Zug (CH)

(*) Notice: Subject to any disclaimer, the term of this patent is extended or adjusted under 35 U.S.C. 154(b) by 496 days.

(21) Appl. No.: 16/925,387

(22) Filed: Jul. 10, 2020

(65) Prior Publication Data

US 2022/0008075 A1 Jan. 13, 2022

(51) Int. Cl.
*A61B 17/064* (2006.01)
*A61B 17/115* (2006.01)
(Continued)

(52) U.S. Cl.
CPC ....... *A61B 17/1155* (2013.01); *A61B 17/1114* (2013.01); *G01L 5/0038* (2013.01); *G01L 5/04* (2013.01); *A61B 2017/00199* (2013.01); *A61B 2017/00398* (2013.01); *A61B 2017/00424* (2013.01); *A61B 2017/00734* (2013.01); *A61B 2017/07228* (2013.01); *A61B 2017/07257* (2013.01); *A61B 2017/07285* (2013.01);
(Continued)

(58) Field of Classification Search
CPC .......................... A61B 17/1114; A61B 17/1155
See application file for complete search history.

(56) References Cited

U.S. PATENT DOCUMENTS

| 5,205,459 A | 4/1993 | Brinkerhoff et al. |
| 5,271,544 A | 12/1993 | Fox et al. |

(Continued)

FOREIGN PATENT DOCUMENTS

| EP | 3078335 A1 | 10/2016 |
| EP | 3381380 A2 | 10/2018 |
| WO | WO 2019/130087 A1 | 7/2019 |

OTHER PUBLICATIONS

International Search Report and Written Opinion dated Nov. 15, 2021, for International Application No. PCT/IB2021/056142, 24 pages.

(Continued)

*Primary Examiner* — Eyamindae C Jallow
(74) *Attorney, Agent, or Firm* — Frost Brown Todd LLC

(57) ABSTRACT

A surgical instrument includes a housing assembly, a movable member, an anvil, and a force sensing assembly. The housing assembly includes a first housing, a second housing, and a deck surface that includes at least one annular array of staple openings. The force sensing assembly includes at least one of a compression force sensor disposed between the first and second housings or a tension force sensor coupled with the movable member or the anvil. The compression force sensor is configured to sense a compression force communicated longitudinally through the first and second housings during at least one of compressing tissue between the anvil and the deck surface or firing the surgical instrument. The tension force sensor is configured to sense a tension force communicated longitudinally through the movable member during at least one of compressing tissue between the anvil and the deck surface or firing the surgical instrument.

20 Claims, 19 Drawing Sheets

(51) Int. Cl.
*A61B 17/11* (2006.01)
*G01L 5/00* (2006.01)
*G01L 5/04* (2006.01)
*A61B 90/00* (2016.01)
*A61B 17/00* (2006.01)
*A61B 17/072* (2006.01)

(52) U.S. Cl.
CPC . *A61B 2090/064* (2016.02); *A61B 2562/0252* (2013.01); *A61B 2562/0261* (2013.01)

(56) References Cited

U.S. PATENT DOCUMENTS

| | | | |
|---|---|---|---|
| 5,275,322 | A | 1/1994 | Brinkerhoff et al. |
| 5,285,945 | A | 2/1994 | Brinkerhoff et al. |
| 5,292,053 | A | 3/1994 | Bilotti et al. |
| 5,333,773 | A | 8/1994 | Main et al. |
| 5,350,104 | A | 9/1994 | Main et al. |
| 5,533,661 | A | 7/1996 | Main et al. |
| 8,910,847 | B2 | 12/2014 | Nalagatla et al. |
| 9,445,816 | B2 | 9/2016 | Swayze et al. |
| 9,463,022 | B2 | 10/2016 | Swayze et al. |
| 9,532,783 | B2 | 1/2017 | Swayze et al. |
| 9,597,081 | B2 | 3/2017 | Swayze et al. |
| 9,713,469 | B2 | 7/2017 | Leimbach et al. |
| 9,907,552 | B2 | 3/2018 | Measamer et al. |
| 9,936,949 | B2 | 4/2018 | Measamer et al. |
| 10,045,780 | B2 | 8/2018 | Adams et al. |
| 10,307,157 | B2 | 6/2019 | Miller et al. |
| 10,709,452 | B2 | 7/2020 | DiNardo et al. |
| 11,219,461 | B2 * | 1/2022 | Eisinger ............ A61B 17/1155 |
| 11,376,006 | B2 * | 7/2022 | Sgroi, Jr. ............ H05K 7/1427 |
| 11,490,891 | B2 * | 11/2022 | Rose ................... A61B 17/072 |
| 2015/0083772 | A1 | 3/2015 | Miller et al. |
| 2017/0258471 | A1 | 9/2017 | DiNardo et al. |
| 2018/0042610 | A1 * | 2/2018 | Sgroi, Jr. ........... A61B 17/3494 |
| 2018/0325517 | A1 | 11/2018 | Wingardner et al. |
| 2018/0368836 | A1 | 12/2018 | Auld et al. |
| 2019/0200981 | A1 * | 7/2019 | Harris ................. A61B 5/0022 |
| 2019/0201136 | A1 | 7/2019 | Shelton, IV et al. |
| 2019/0206569 | A1 | 7/2019 | Shelton, IV et al. |
| 2020/0093487 | A1 | 3/2020 | Baber et al. |
| 2020/0100830 | A1 | 4/2020 | Henderson et al. |
| 2020/0113565 | A1 | 4/2020 | Bakos et al. |
| 2020/0337706 | A1 * | 10/2020 | Truckai .............. A61B 18/1482 |
| 2021/0077093 | A1 | 3/2021 | Adams et al. |
| 2021/0077110 | A1 | 3/2021 | Adams et al. |
| 2021/0077112 | A1 * | 3/2021 | Adams ................ A61B 17/1114 |

OTHER PUBLICATIONS

U.S. Appl. No. 16/887,182, entitled "Shaft Attachment Feature for Circular Surgical Stapler," filed May 29, 2020.

U.S. Appl. No. 16/925,448, entitled "Load Sensor for Circular Surgical Stapler," filed Jul. 10, 2020.

U.S. Appl. No. 63/018,664, entitled "Stabilizer for Surgical Shafts or Cannulas," filed May 1, 2020.

* cited by examiner

COMPRESSION AND FIRING FORCE SENSOR FOR CIRCULAR SURGICAL STAPLER

BACKGROUND

Examples of circular staplers are described in U.S. Pat. No. 5,205,459, entitled "Surgical Anastomosis Stapling Instrument," issued Apr. 27, 1993; U.S. Pat. No. 5,271,544, entitled "Surgical Anastomosis Stapling Instrument," issued Dec. 21, 1993; U.S. Pat. No. 5,275,322, entitled "Surgical Anastomosis Stapling Instrument," issued Jan. 4, 1994; U.S. Pat. No. 5,285,945, entitled "Surgical Anastomosis Stapling Instrument," issued Feb. 15, 1994; U.S. Pat. No. 5,292,053, entitled "Surgical Anastomosis Stapling Instrument," issued Mar. 8, 1994; U.S. Pat. No. 5,333,773, entitled "Surgical Anastomosis Stapling Instrument," issued Aug. 2, 1994; U.S. Pat. No. 5,350,104, entitled "Surgical Anastomosis Stapling Instrument," issued Sep. 27, 1994; and U.S. Pat. No. 5,533,661, entitled "Surgical Anastomosis Stapling Instrument," issued Jul. 9, 1996; and U.S. Pat. No. 8,910,847, entitled "Low Cost Anvil Assembly for a Circular Stapler," issued Dec. 16, 2014. The disclosure of each of the above-cited U.S. patents is incorporated by reference herein.

Some circular staplers may include a motorized actuation mechanism. Examples of circular staplers with motorized actuation mechanisms are described in U.S. Pub. No. 2015/0083772, entitled "Surgical Stapler with Rotary Cam Drive and Return," published Mar. 26, 2015 (now abandoned); U.S. Pat. No. 9,936,949, entitled "Surgical Stapling Instrument with Drive Assembly Having Toggle Features," issued Apr. 10, 2018; U.S. Pat. No. 9,907,552, entitled "Control Features for Motorized Surgical Stapling Instrument," issued Mar. 6, 2018; and U.S. Pat. No. 9,713,469, entitled "Surgical Stapler with Rotary Cam Drive," issued Jul. 25, 2017. The disclosure of each of the above-cited U.S. Patent Publication and U.S. patents is incorporated by reference herein.

While various kinds of surgical stapling instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
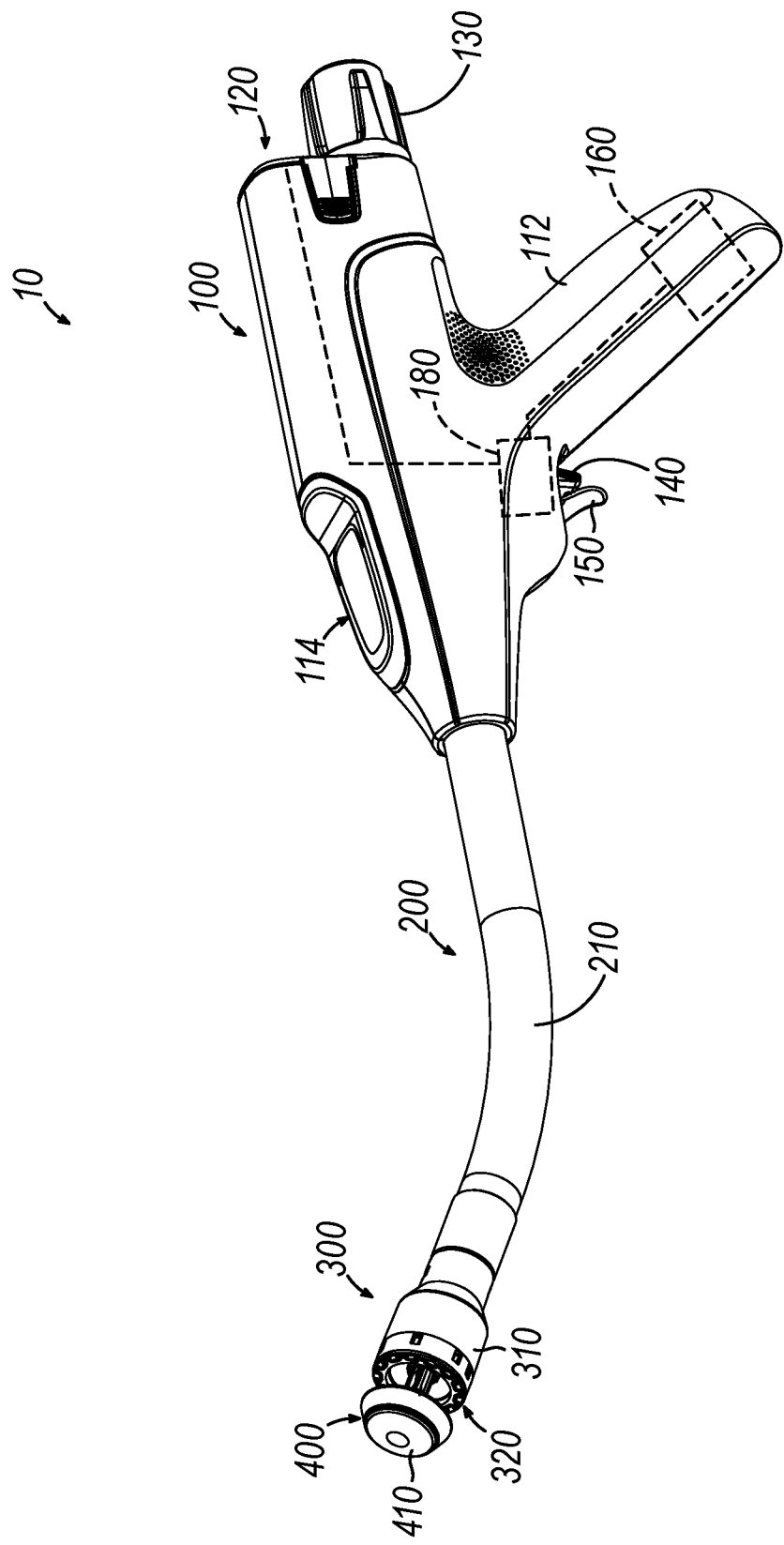
FIG. 1 depicts a perspective view of an exemplary circular surgical stapler.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "top," "bottom," "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

I. Overview of Exemplary Circular Surgical Stapling Instrument

Figure 2:
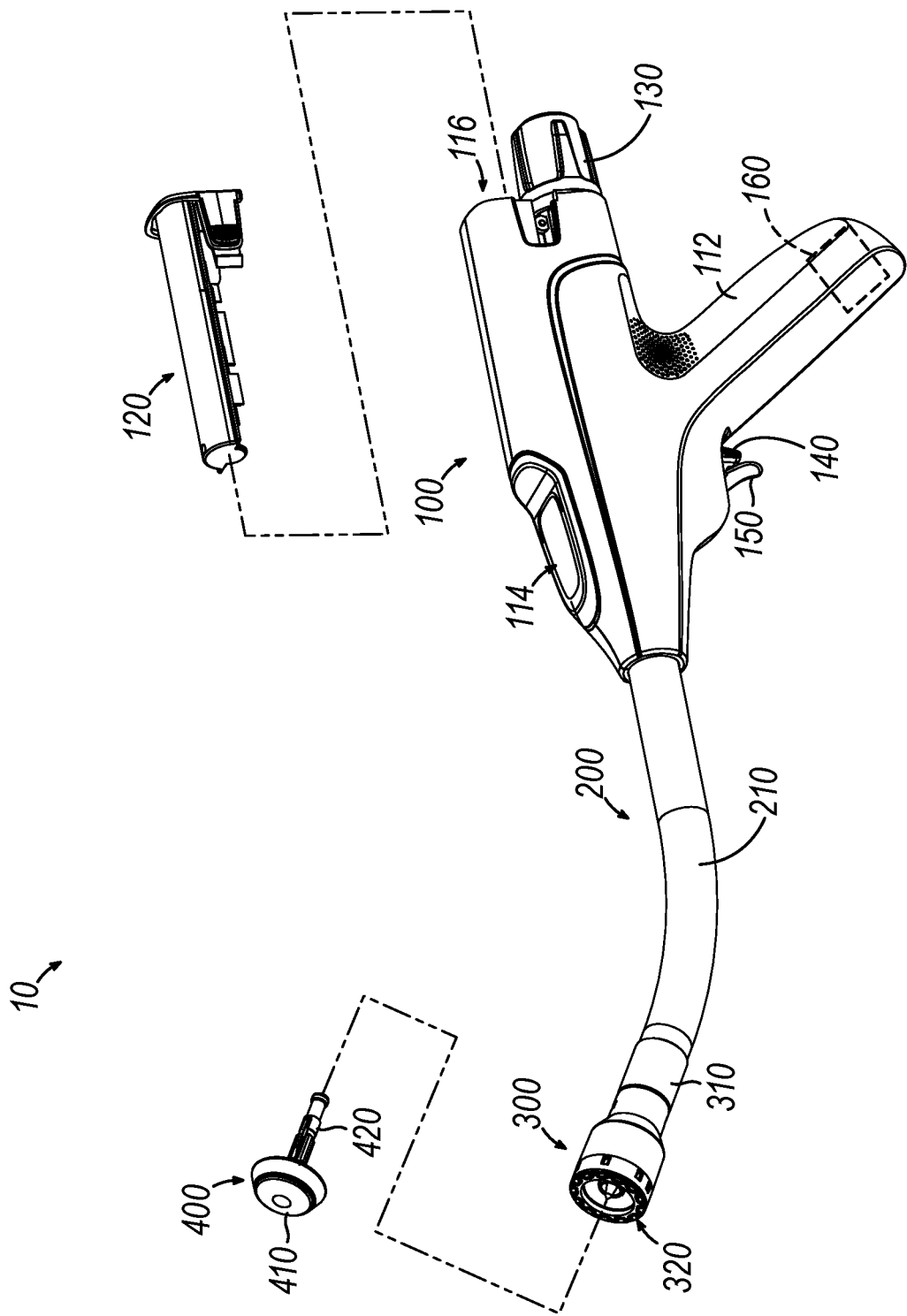
FIG. 2 depicts a perspective view of the circular stapler of FIG. 1, with a battery pack removed from a handle assembly and an anvil removed from a stapling head assembly.

FIGS. 1-2 depict an exemplary circular surgical stapling instrument (10) that may be used to provide an end-to-end, side-to-side, or end-to-side anastomosis between two sections of an anatomical lumen such as a portion of a patient's digestive tract. Instrument (10) of this example includes a body assembly (e.g. a handle assembly (100)), a shaft assembly (200) extending distally from handle assembly (100), a stapling head assembly (300) at a distal end of shaft assembly (200), and an anvil (400) configured to releasably couple and cooperate with stapling head assembly (300) to clamp, staple, and cut tissue. Instrument (10) further includes a removable battery pack (120) operable to provide electrical power to a motor (160) housed within handle assembly (100), as will be described in greater detail below.

Shaft assembly (200) extends distally from handle assembly (100) and includes a preformed bend. Stapling head assembly (300) is located at the distal end of shaft assembly (200). As shown in FIGS. 1-2 and as will be described in greater detail below, anvil (400) is configured to removably couple with shaft assembly (200), adjacent to stapling head assembly (300). As will also be described in greater detail below, anvil (400) and stapling head assembly (300) are configured to cooperate to manipulate tissue in three ways, including clamping the tissue, cutting the tissue, and stapling the tissue. A knob (130) at the proximal end of handle assembly (100) is rotatable relative to casing (110) to provide precise clamping of the tissue between anvil (400) and stapling head assembly (300). When a safety trigger (140) of handle assembly (100) is pivoted away from a firing trigger (150) of handle assembly (100), firing trigger (150) may be actuated to thereby provide cutting and stapling of the tissue.

A. Exemplary Anvil

Figure 3:
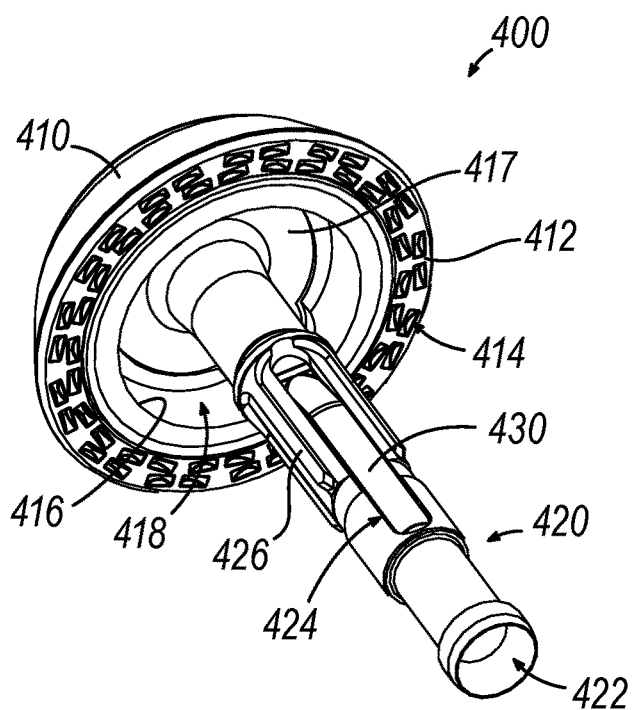
FIG. 3 depicts a perspective view of the anvil of the circular stapler of FIG. 1.

As best seen in FIG. 3, anvil (400) of the present example comprises a head (410) and a shank (420). Head (410) includes a proximal surface (412) that defines a plurality of staple forming pockets (414). Staple forming pockets (414) are arranged in two concentric annular arrays in the present example. Staple forming pockets (414) are configured to deform staples as the staples are driven into staple forming pockets (414). Proximal surface (412) terminates at an inner edge (416), which defines an outer boundary of an annular recess (418) surrounding shank (420).

Shank (420) defines a bore (422) and includes a pair of pivoting latch members (430). Latch members (430) are positioned within bore (422) such that distal ends (434) are positioned at the proximal ends of lateral openings (424), which are formed through the sidewall of shank (420). Latch members (430) thus act as retaining clips. This allows anvil (400) to be removably secured to an actuatable closure member in the form of a trocar (330) of stapling head assembly (300), as will be described in greater detail below.

B. Exemplary Stapling Head Assembly

Figure 4:
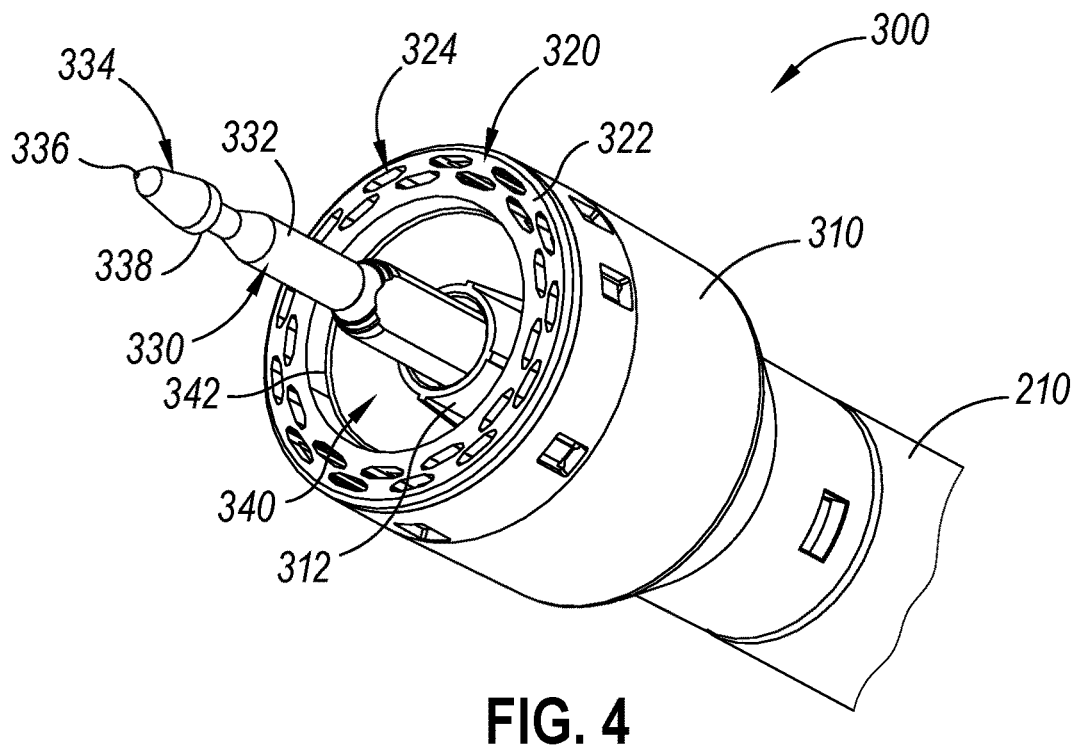
FIG. 4 depicts a perspective view of the stapling head assembly of the circular stapler of FIG. 1.
Figure 5:
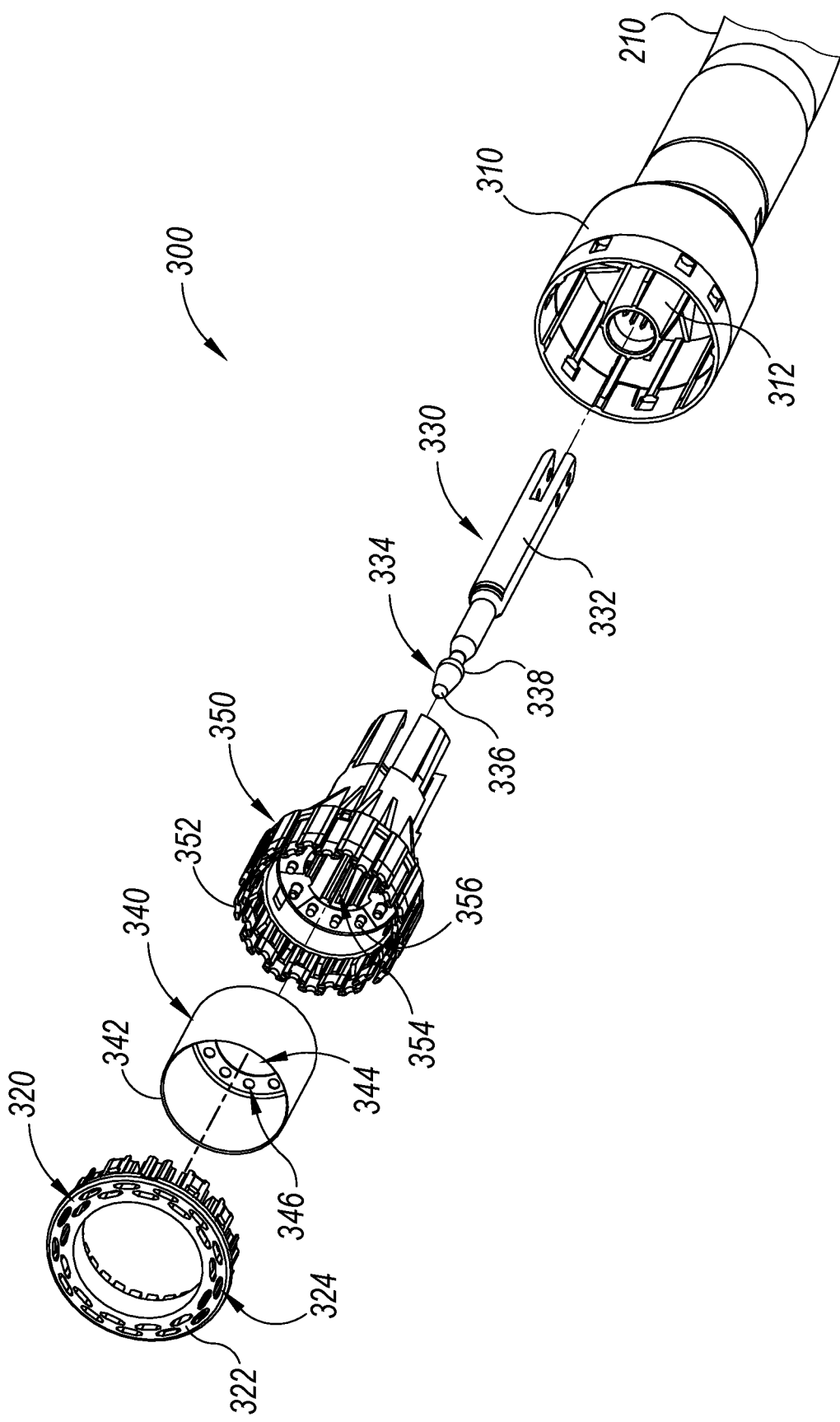
FIG. 5 depicts an exploded perspective view of the stapling head assembly of FIG. 4.

As best seen in FIGS. 4 and 5, stapling head assembly (300) of the present example is coupled to a distal end of shaft assembly (200) and comprises a body member (310) and a staple driver member (350) slidably housed therein. Body member (310) includes a distally extending cylindraceous inner core member (312). Body member (310) is fixedly secured to an outer sheath (210) of shaft assembly (200), and body member (310) and outer sheath (210) thus serve together as a mechanical ground for stapling head assembly (300).

Trocar (330) is positioned coaxially within inner core member (312) of body member (310). As will be described in greater detail below, trocar (330) is operable to translate distally and proximally relative to body member (310) in response to rotation of knob (130) relative to casing (110) of handle assembly (100). Trocar (330) comprises a shaft (332) and a head (334). Head (334) includes a pointed tip (336) and an inwardly extending proximal surface (338). Head (334) and the distal portion of shaft (332) are configured for insertion in bore (422) of anvil (400). Proximal surface (338) and latch shelves (436) have complementary positions and configurations such that latch shelves (436) engage proximal surface (338) when shank (420) of anvil (400) is fully seated on trocar (330). Anvil (400) is thus secured to trocar (330) through a snap fit provided by latch members (430).

Staple driver member (350) is operable to actuate longitudinally within body member (310) in response to activation of motor (160) as will be described in greater detail below. Staple driver member (350) of the present example includes two distally presented concentric annular arrays of staple drivers (352). Staple drivers (352) are arranged to correspond with the arrangement of staple forming pockets (414) of anvil (400). Thus, each staple driver (352) is configured to drive a corresponding staple into a corresponding staple forming pocket (414) when stapling head assembly (300) is actuated. Staple driver member (350) also defines a bore (354) that is configured to coaxially receive core member (312) of body member (310). An annular array of studs (356) project distally from a distally presented surface surrounding bore (354).

A cylindraceous knife member (340) is coaxially positioned within staple driver member (350). Knife member (340) includes a distally presented, sharp circular cutting edge (342). Knife member (340) is sized such that knife member (340) defines an outer diameter that is smaller than the diameter defined by the inner annular array of staple drivers (352). Knife member (340) also defines an opening that is configured to coaxially receive core member (312) of body member (310). An annular array of openings (346) formed in knife member (340) is configured to complement the annular array of studs (356) of staple driver member (350), such that knife member (340) is fixedly secured to staple driver member (350) via studs (356) and openings (346).

Figure 9:
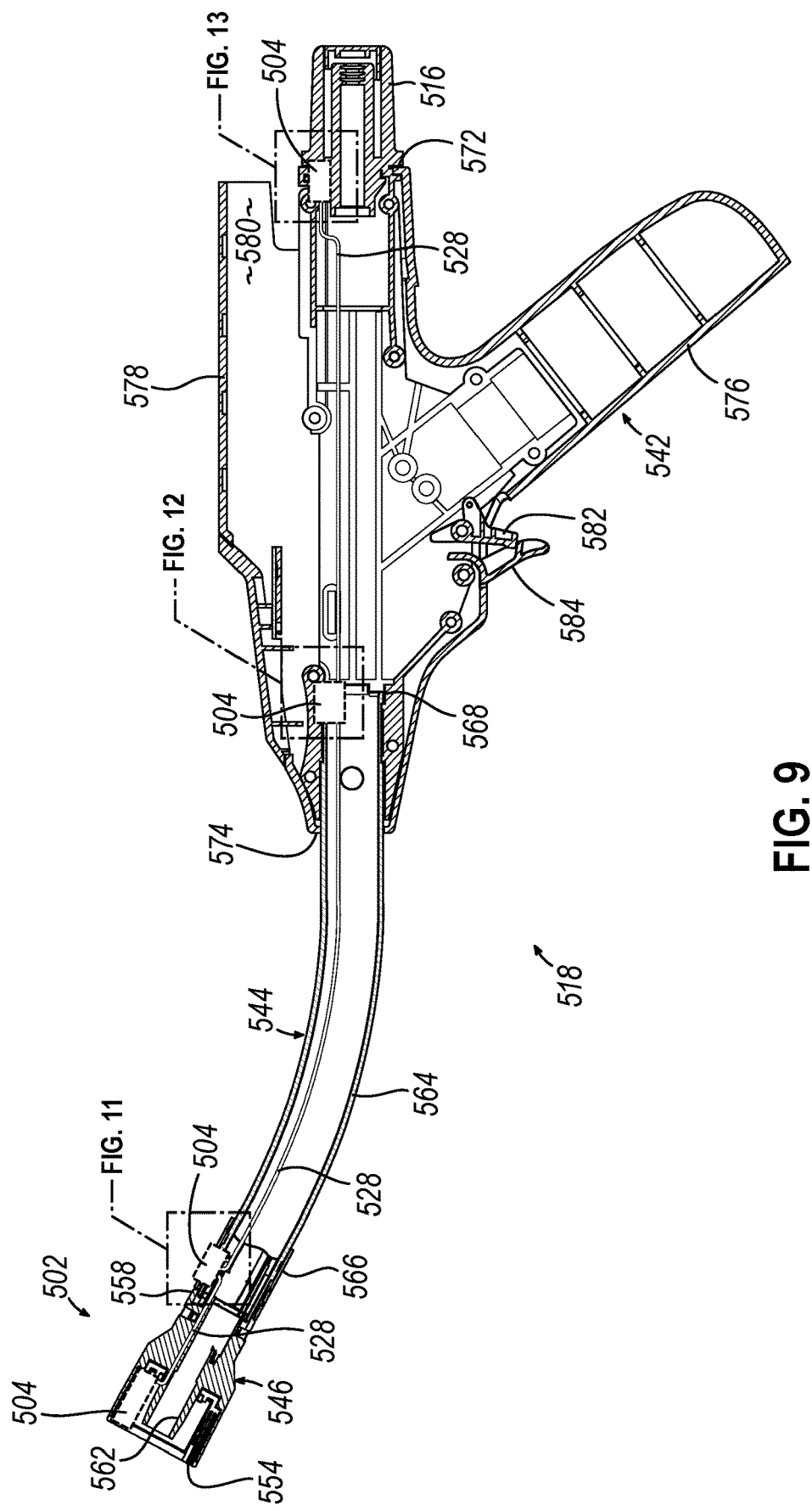
FIG. 9 depicts a cross-sectional view of a housing assembly of the circular surgical stapler of FIG. 8, with the housing assembly including a casing, an outer shaft, a handle assembly, and an actuator.

A deck member (320) is fixedly secured to a distal end of body member (310). Deck member (320) includes a distally presented deck surface (322) defining two concentric annular arrays of staple openings (324). Staple openings (324) are arranged to correspond with the arrangement of staple drivers (352) and staple forming pockets (414) described above. Thus, each staple opening (324) is configured to provide a path for a corresponding staple driver (352) to drive a corresponding staple through deck member (320) and into a corresponding staple forming pocket (414) when stapling head assembly (300) is actuated. As best seen in FIG. 9, deck member (320) defines an inner diameter that is just slightly larger than the outer diameter defined by knife member (340). Deck member (320) is thus configured to allow knife member (340) to translate distally to a point where cutting edge (342) is distal to deck surface (322).

C. Exemplary Shaft Assembly

Figure 6:
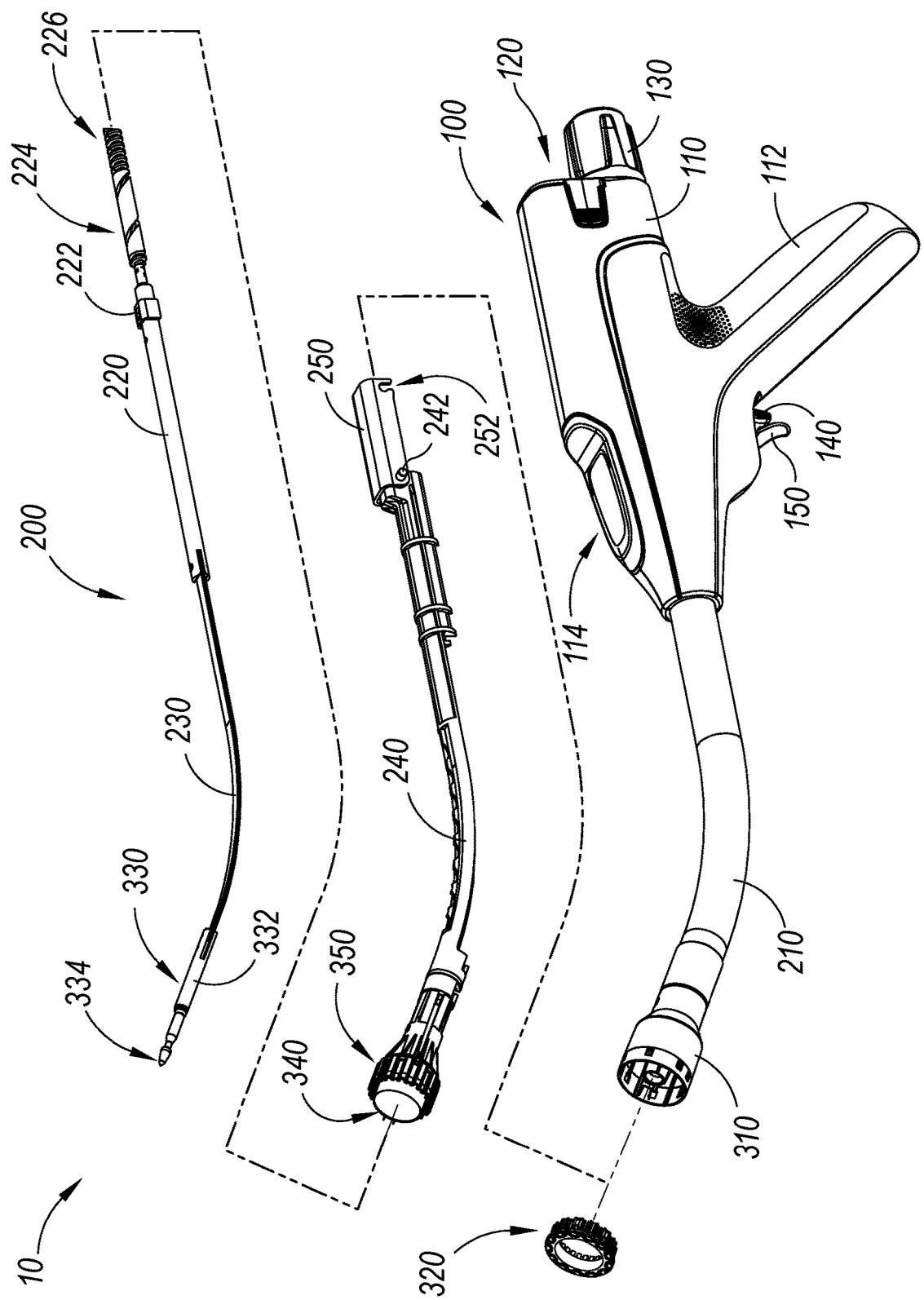
FIG. 6 depicts an exploded perspective view of the circular stapler of FIG. 1, with portions of the shaft assembly shown separated from each other.

FIG. 6 shows various components of shaft assembly (200), which couples components of stapling head assembly (300) with components of handle assembly (100). In particular, and as noted above, shaft assembly (200) includes an outer sheath (210) that extends between handle assembly (100) and body member (310). Shaft assembly (200) further includes a trocar actuation rod (220) and a trocar actuation band assembly (230). The distal end of trocar actuation band assembly (230) is fixedly secured to the proximal end of trocar shaft (332). The proximal end of trocar actuation band assembly (230) is fixedly secured to the distal end of trocar actuation rod (220). It should therefore be understood that trocar (330) will translate longitudinally relative to outer sheath (210) in response to translation of trocar actuation band assembly (230) and trocar actuation rod (220) relative to outer sheath (210). A clip (222) is fixedly secured to trocar actuation rod (220) and is configured to cooperate with complementary features within handle assembly (100) to prevent trocar actuation rod (220) from rotating within handle assembly (100) while still permitting trocar actuation rod (220) to translate longitudinally within handle assembly (100). Trocar actuation rod (220) further includes a coarse helical threading (224) and a fine helical threading (226).

Shaft assembly (200) further includes a stapling head assembly driver (240) that is slidably received within outer sheath (210). The distal end of stapling head assembly driver (240) is fixedly secured to the proximal end of staple driver member (350). The proximal end of stapling head assembly driver (240) is secured to a drive bracket (250) via a pin (242). It should therefore be understood that staple driver member (350) will translate longitudinally relative to outer sheath (210) in response to translation of stapling head assembly driver (240) and drive bracket (250) relative to outer sheath (210).

D. Exemplary Handle Assembly and User Input Features

As shown in FIG. 1, handle assembly (100) includes a casing (110) having a lower portion that defines an obliquely oriented pistol grip (112) and an upper portion that supports a user interface feature (114) and receives a battery pack (120), as described in greater detail below. Handle assembly (100) further includes several features that are operable to actuate anvil (400) and stapling head assembly (300). In particular, handle assembly (100) includes a rotatable knob (130), a safety trigger (140) a firing trigger (150), a motor (160), and a motor activation module (180). Knob (130) is coupled with trocar actuation rod (220) via a nut (not shown), such that coarse helical threading (224) will selectively engage a thread engagement feature within the interior of the nut; and such that fine helical threading (226) will selectively engage a thread engagement feature within the interior of knob (130). These complementary structures are configured such that trocar actuation rod (220) will first translate proximally at a relatively slow rate, then translate proximally at a relatively fast rate, in response to rotation of knob (130).

It should be understood that when anvil (400) is coupled with trocar (330), rotation of knob (130) will provide corresponding translation of anvil (400) relative to stapling head assembly (300). It should also be understood that knob (130) may be rotated in a first angular direction (e.g., clockwise) to retract anvil (400) toward stapling head assembly (300); and in a second angular direction (e.g., counterclockwise) to advance anvil (400) away from stapling head assembly (300). Knob (130) may thus be used to adjust a gap distance (d) between opposing surfaces (412, 322) of anvil (400) and stapling head assembly (300) until a suitable gap distance (d) has been achieved, for example as shown in FIG. 7C described below.

Firing trigger (150) is operable to activate motor (160) to thereby actuate stapling head assembly (300). Safety trigger (140) is operable to selectively block actuation of firing trigger (150) based on the longitudinal position of anvil (400) in relation to stapling head assembly (300). Handle assembly (100) also includes components that are operable to selectively lock out both triggers (140, 150) based on the position of anvil (400) relative to stapling head assembly (300). For instance, safety trigger (140) may be blocked from rotating from an engaged position to a disengaged position until the position of anvil (400) relative to stapling head assembly (300) is within a predefined range. Accordingly, until the anvil position is within the predefined range, actuation of firing trigger (150) is blocked by safety trigger (140), thereby inhibiting firing of stapling head assembly (300).

Firing trigger (150) is operable to actuate a switch of motor activation module (180) (FIG. 1) when firing trigger (150) is pivoted to a fired position. Motor activation module (180) is in communication with battery pack (120) and motor (160), such that motor activation module (180) is configured to provide activation of motor (160) with electrical power from battery pack (120) in response to the paddle actuating the switch of motor activation module (180). Thus, motor (160) will be activated when firing trigger (150) is pivoted. This activation of motor (160) will actuate stapling head assembly (300) via drive bracket (250), as described in greater detail below. As best shown in FIGS. 1-2, handle assembly (100) is further configured to releasably receive a battery pack (120) that is operable to provide electrical power to motor (160), as noted above.

E. Exemplary Anastomosis Procedure with Circular Stapling Instrument

FIGS. 7A-7E show instrument (10) being used to form an anastomosis (70) between two tubular anatomical structures (20, 40). By way of example only, the tubular anatomical structures (20, 40) may comprise sections of a patient's esophagus, sections of a patient's colon, other sections of the patient's digestive tract, or any other tubular anatomical structures.

Figure 7A:
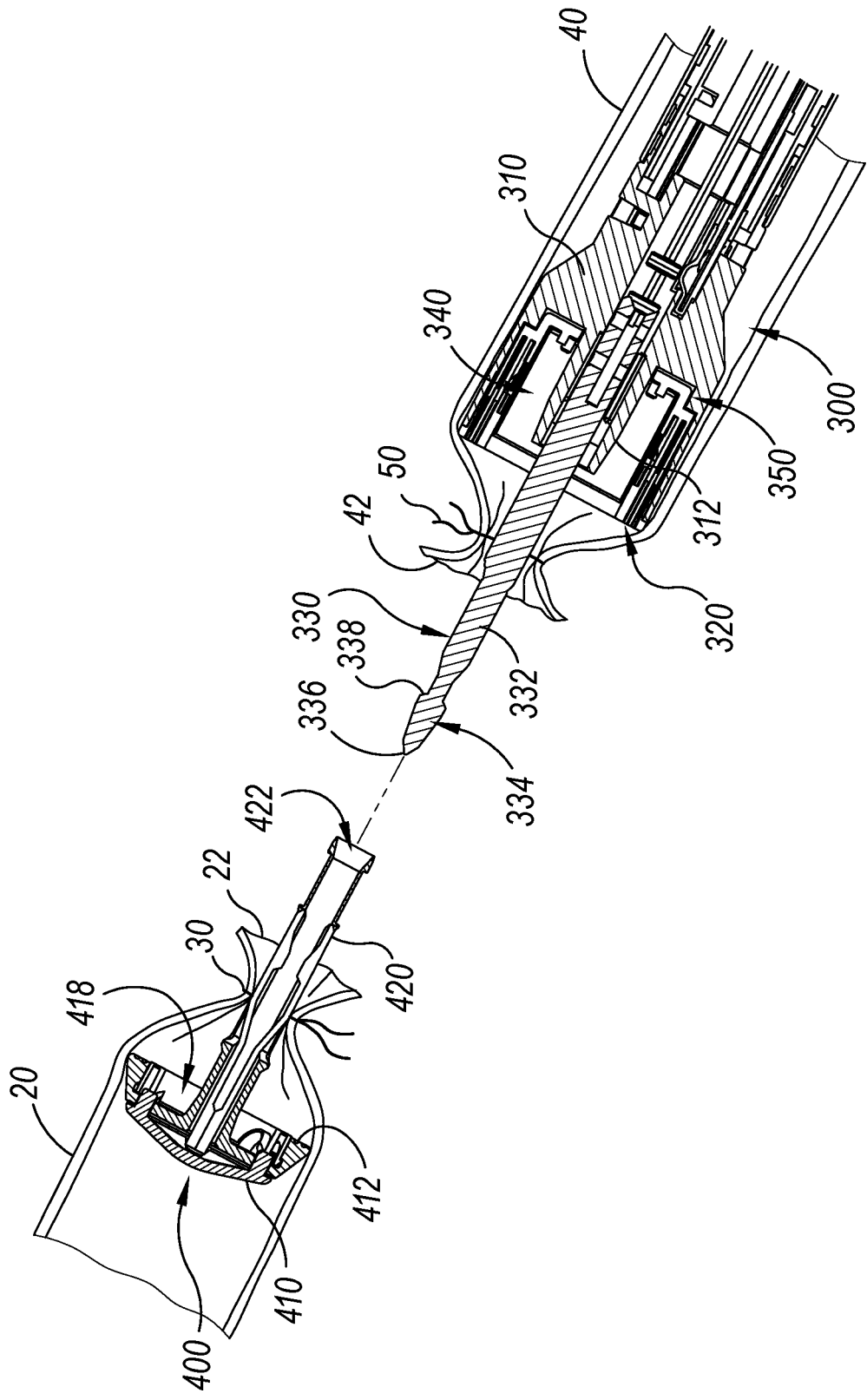
FIG. 7A depicts a cross-sectional side view of the anvil of FIG. 3 positioned within a first section of a digestive tract and the stapling head assembly of FIG. 4 positioned in a second section of the digestive tract, with the anvil separated from the stapling head assembly.

As shown in FIG. 7A, anvil (400) is positioned in one tubular anatomical structure (20) and stapling head assembly (300) is positioned in another tubular anatomical structure (40). As shown in FIG. 7A, anvil (400) is positioned in tubular anatomical structure (20) such that shank (420)

protrudes from the open severed end (22) of tubular anatomical structure (20). In the present example, purse-string suture (30) is provided about a mid-region of shank (420) to generally secure the position of anvil (400) in tubular anatomical structure (20). Stapling head assembly (300) is positioned in tubular anatomical structure (40) such that trocar (330) protrudes from the open severed end (42) of tubular anatomical structure (20). A purse-string suture (50) is provided about a mid-region of shaft (332) to generally secure the position of stapling head assembly (300) in tubular anatomical structure (40). Stapling head assembly (300) is then urged distally to ensure that stapling head assembly (300) is fully seated at the distal end of tubular anatomical structure (40).

Figure 7B:
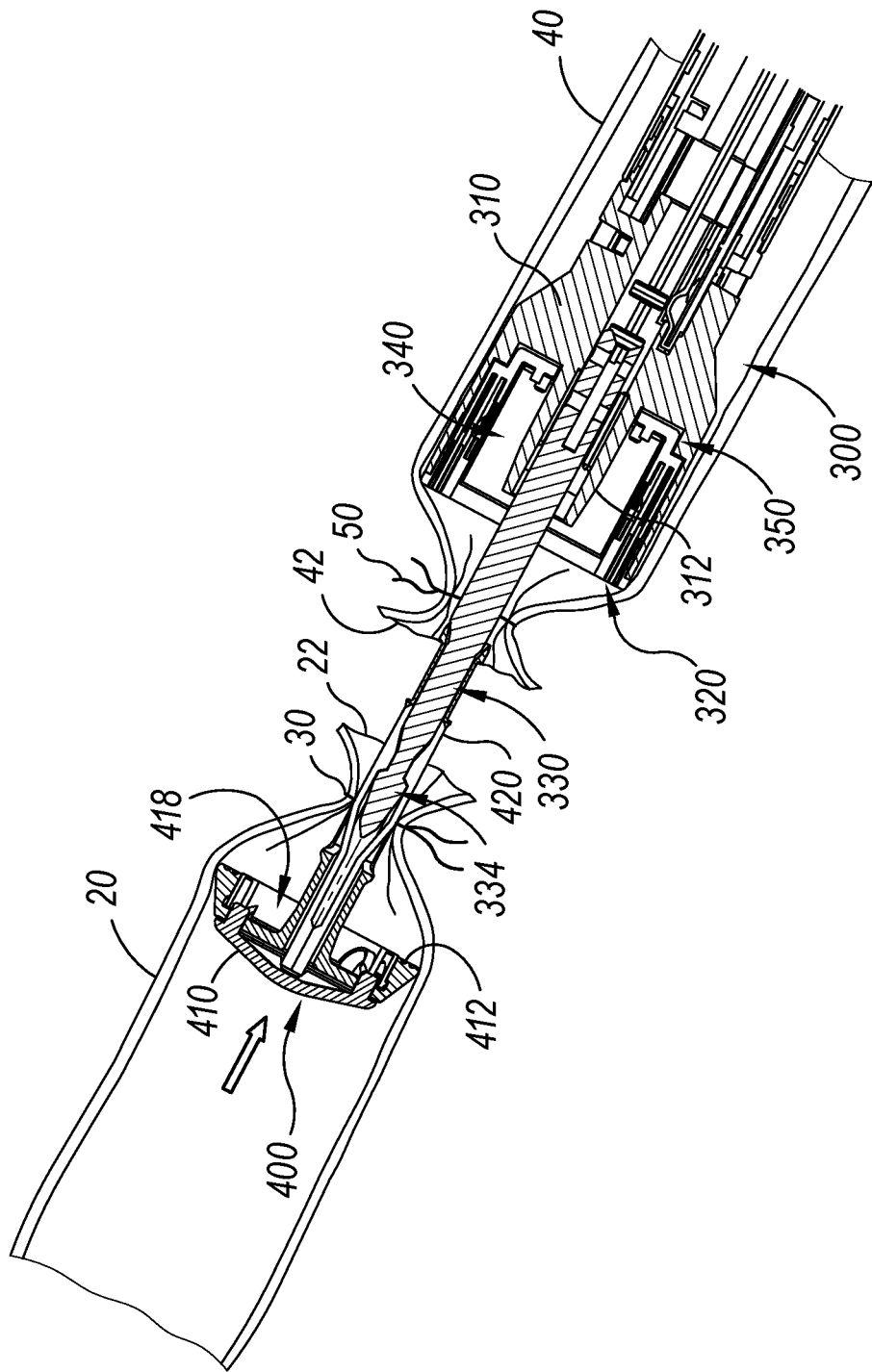
FIG. 7B depicts a cross-sectional side view of the anvil of FIG. 3 positioned within the first section of the digestive tract and the stapling head assembly of FIG. 4 positioned in the second section of the digestive tract, with the anvil secured to the stapling head assembly.
Figure 7C:
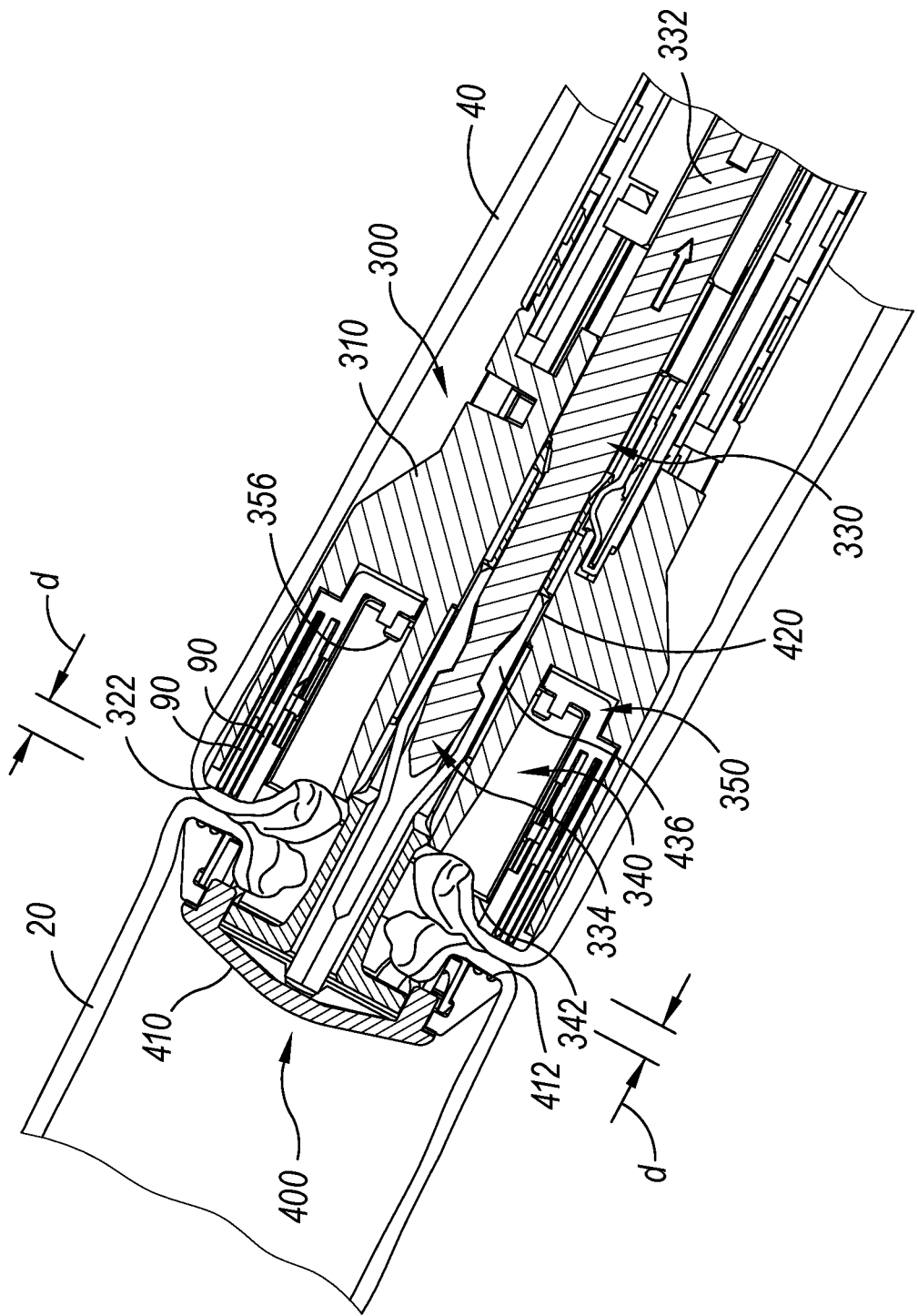
FIG. 7C depicts a cross-sectional side view of the anvil of FIG. 3 positioned within the first section of the digestive tract and the stapling head assembly of FIG. 4 positioned in the second section of the digestive tract, with the anvil retracted toward the stapling head assembly to thereby clamp tissue between the anvil and the stapling head assembly.

Next, anvil (400) is secured to trocar (330) by inserting trocar (330) into bore (422) as shown in FIG. 7B. Latch members (430) engage head (334) of trocar (330), thereby providing a secure fit between anvil (400) and trocar (330). The operator then rotates knob (130) while holding casing (110) stationary via pistol grip (112). This rotation of knob (130) causes trocar (330) and anvil (400) to retract proximally. As shown in FIG. 7C, this proximal retraction of trocar (330) and anvil (400) compresses the tissue of tubular anatomical structures (20, 40) between surfaces (412, 322) of anvil (400) and stapling head assembly (300). As this occurs, the operator may observe the tactile resistance or feedback via knob (130) while turning knob (130), with such tactile resistance or feedback indicating that the tissue is being compressed. As the tissue is being compressed, the operator may visually observe the position of an indicator needle (522) within a user interface feature (114) of handle assembly (100) to determine whether the gap distance (d) between opposing surfaces (412, 322) of anvil (400) and stapling head assembly (300) is appropriate; and make any necessary adjustments via knob (130).

Figure 7D:
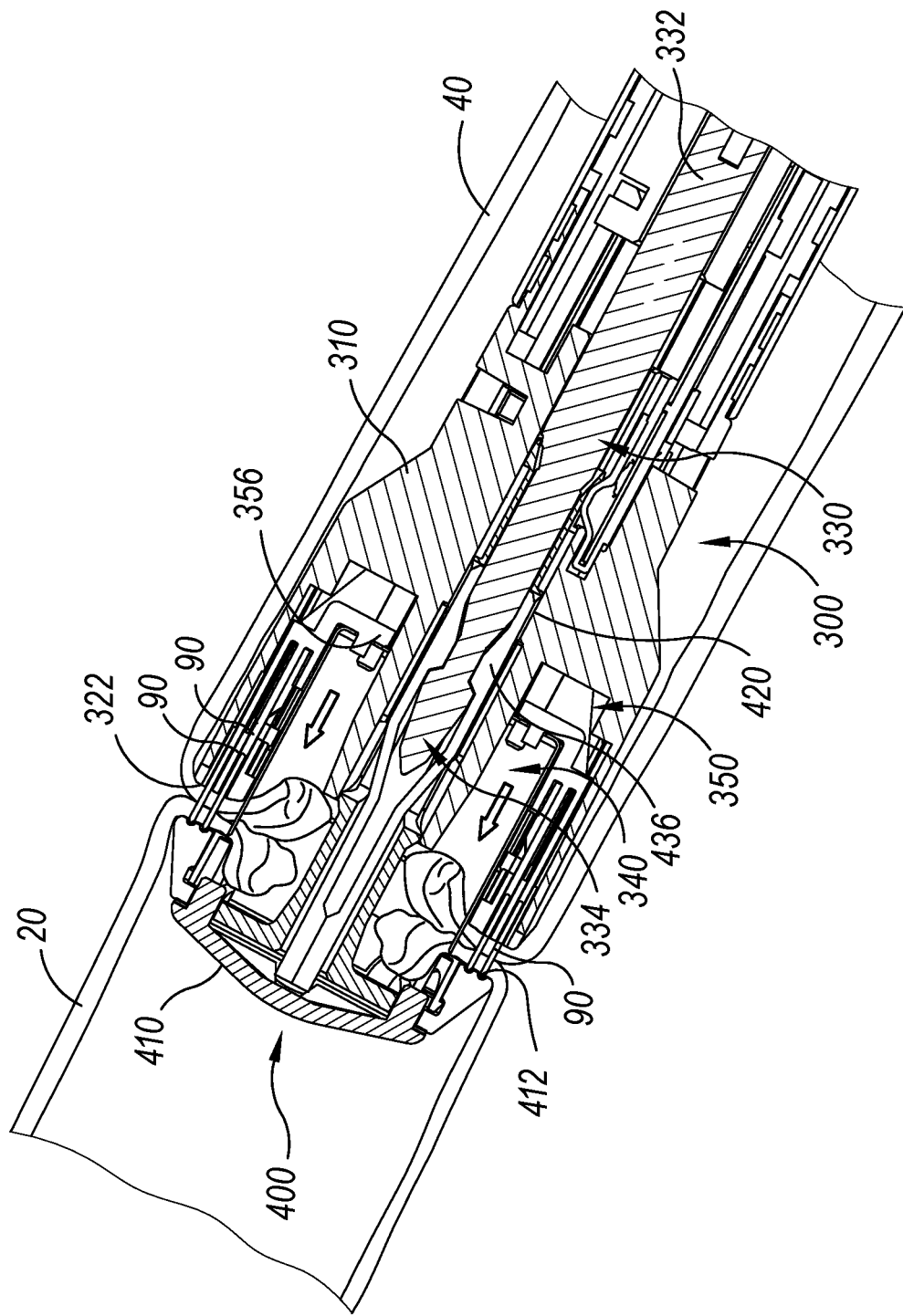
FIG. 7D depicts a cross-sectional side view of the anvil of FIG. 3 positioned within the first section of the digestive tract and the stapling head assembly of FIG. 4 positioned in the second section of the digestive tract, with the stapling head assembly actuated to sever and staple the clamped tissue.

Once the operator has appropriately set the gap distance (d) via knob (130), the operator pivots safety trigger (140) toward pistol grip (112) to enable actuation of firing trigger (150). The operator then pivots firing trigger (150) toward pistol grip (112), thus causing paddle (158) to actuate the switch of motor activation module (180) and thereby activate motor (160) to rotate. This rotation of motor (160) causes actuation (or "firing") of stapling head assembly (300) by actuating drive bracket (250) distally to thereby drive knife member (340) and staple driver member (350) distally, as shown in FIG. 7D. As knife member (340) translates distally, cutting edge (342) of knife member (340) cuts excess tissue that is positioned within annular recess (418) of anvil (400) and the interior of knife member (340).

As shown in FIG. 3, anvil (400) of the present example includes a breakable washer (417) positioned within annular recess (418). This washer (417) is broken by knife member (340) when the knife member (340) completes a full distal range of motion from the position shown in FIG. 7C to the position shown in FIG. 7D. In versions where washer (417) is included, it should be understood that washer (417) may also serve as a cutting board for knife member (340) to assist in cutting of tissue. As staple driver member (350) translates distally from the position shown in FIG. 7C to the position shown in FIG. 7D, staple driver member (350) drives staples (90) through the tissue of tubular anatomical structures (20, 40) and into staple forming pockets (414) of anvil (400). Staple forming pockets (414) deform the driven staples (90) into a "B" shape or a three-dimensional shape, for example, such that the formed staples (90) secure the ends of tissue together, thereby coupling tubular anatomical structure (20) with tubular anatomical structure (40).

Figure 7E:
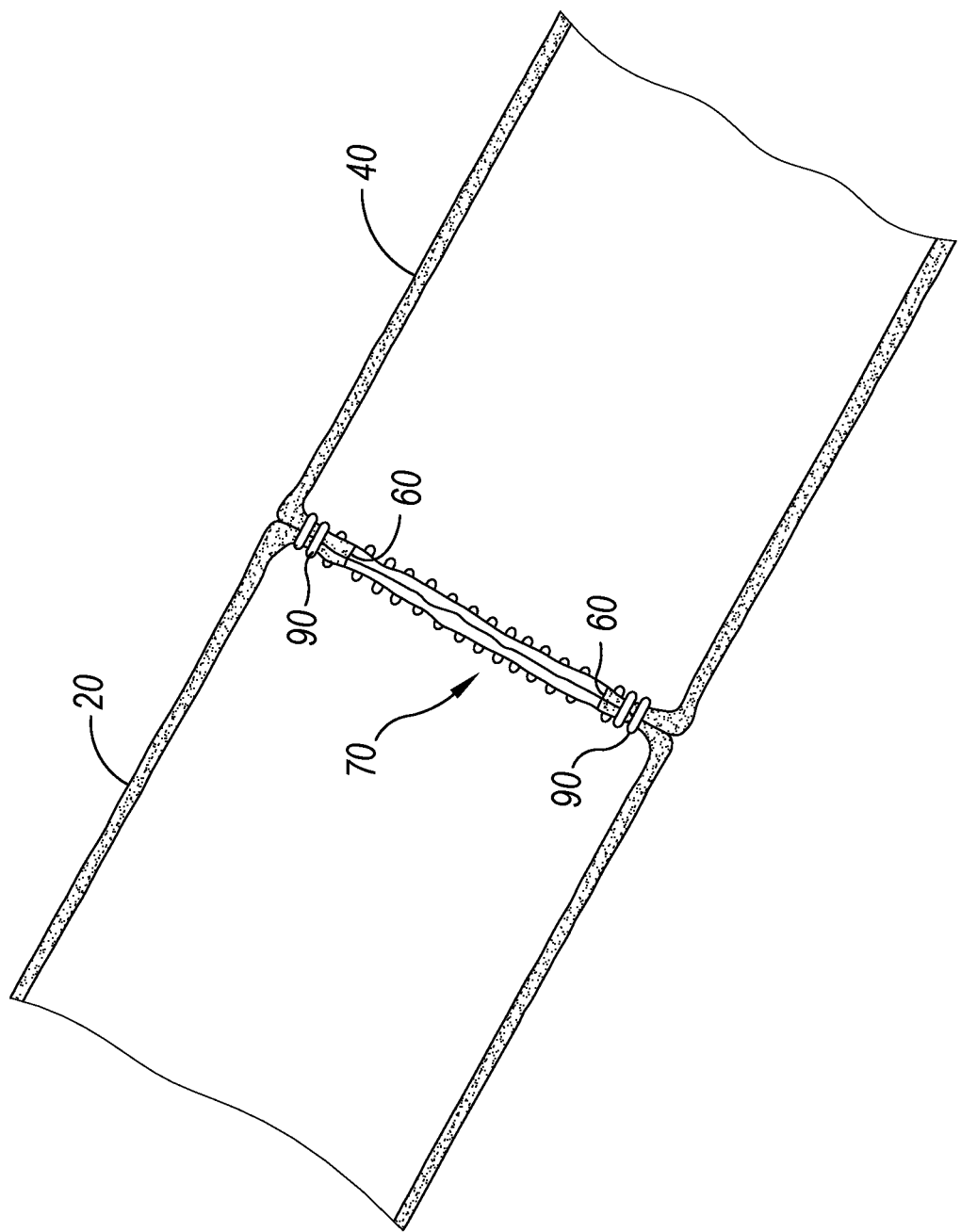
FIG. 7E depicts a cross-sectional side view of the first and second sections of the digestive tract of FIG. 7A joined together at an end-to-end anastomosis.

After the operator has actuated stapling head assembly (300) as shown in FIG. 7D, the operator rotates knob (130) to drive anvil (400) distally away from stapling head assembly (300), increasing the gap distance (d) to facilitate release of the tissue between surfaces (412, 322). The operator then removes instrument (10) from the patient, with anvil (400) still secured to trocar (330). With instrument (10) removed, the tubular anatomical structures (20, 40) are left secured together by two annular arrays of staples (90) at an anastomosis (70) as shown in FIG. 7E. The inner diameter of the anastomosis (70) is defined by the severed edge (60) left by knife member (340).

II. Exemplary Circular Surgical Stapling Instrument with Force Sensing Assembly

A. Overview

Applying an appropriate amount of tissue compression before firing (i.e., pre-fire tissue compression) and/or an appropriate amount of force to fire instrument (10) may improve staple formation. As used herein, firing is the distal actuation of the staples and the knife (e.g., knife member (340)) into the clamped tissue, and pre-fire tissue compression is the tissue compression that occurs prior to firing (i.e., the distal actuation of the staples and the knife into the clamped tissue). The pre-fire tissue compression of instrument (10) is generally depicted in FIG. 7C described above, and the firing of instrument (10) is generally depicted in FIG. 7D described above. Applying the appropriate amount of force may be beneficial for both manual circular staplers and powered circular staplers. Additionally, it may be desirable to monitor such forces experienced by and communicated through instrument (10) to evaluate their effects on performance and lifespan of instrument (10). It would therefore be beneficial to determine the pre-fire tissue compression force and/or the force to fire instrument (10) using actual data from instrument (10) as tissue thickness may vary from patient to patient, which may vary the desired amount of compression force.

It may also be desirable to provide a version of circular surgical stapling instrument (10) that determines the pre-fire tissue compression force and/or the force to fire instrument (10), and conveys this information to the user and/or combines the information with other information from other stapling procedures. Obtaining real time data may allow the user to take actions to improve staple formation. Additionally, assessing data from multiple instruments may allow for trends to be ascertained and alterations to be implemented. This may allow instrument (10) to provide a more consistent pre-firing tissue compression force and/or force to fire. Measuring and tracking the pre-fire tissue compression force and/or the force to fire of instrument (10) may therefore be beneficial to the user during the procedure and to the user(s) after the procedure.

Furthermore, it may be desirable to provide such a version of instrument (10) that determines this data without directly measuring the pre-fire tissue compression force and the force to fire at the distal end of instrument (10). Indirect measurement of actual pre-fire tissue compression force and/or the force to fire may eliminate to need to route one or more wires through at least portions of shaft assembly (200) and stapling head assembly (300) to connect a sensor with a control system. For example, it may be difficult to route one or more wires between deck surface (322) of deck member (320) and proximal surface (412) of anvil (400). It may therefore be additionally desirable to place one or more sensors outside of the distal end of instrument (10) to indirectly determine pre-fire tissue compression force and/or the force to fire using analysis of actual tension and compression forces experienced by instrument (10).

The below description provides several examples of variations of instrument (10) that provide the various force sensing features and capabilities described above.

B. Exemplary Circular Surgical Stapling Instrument

Figure 8:
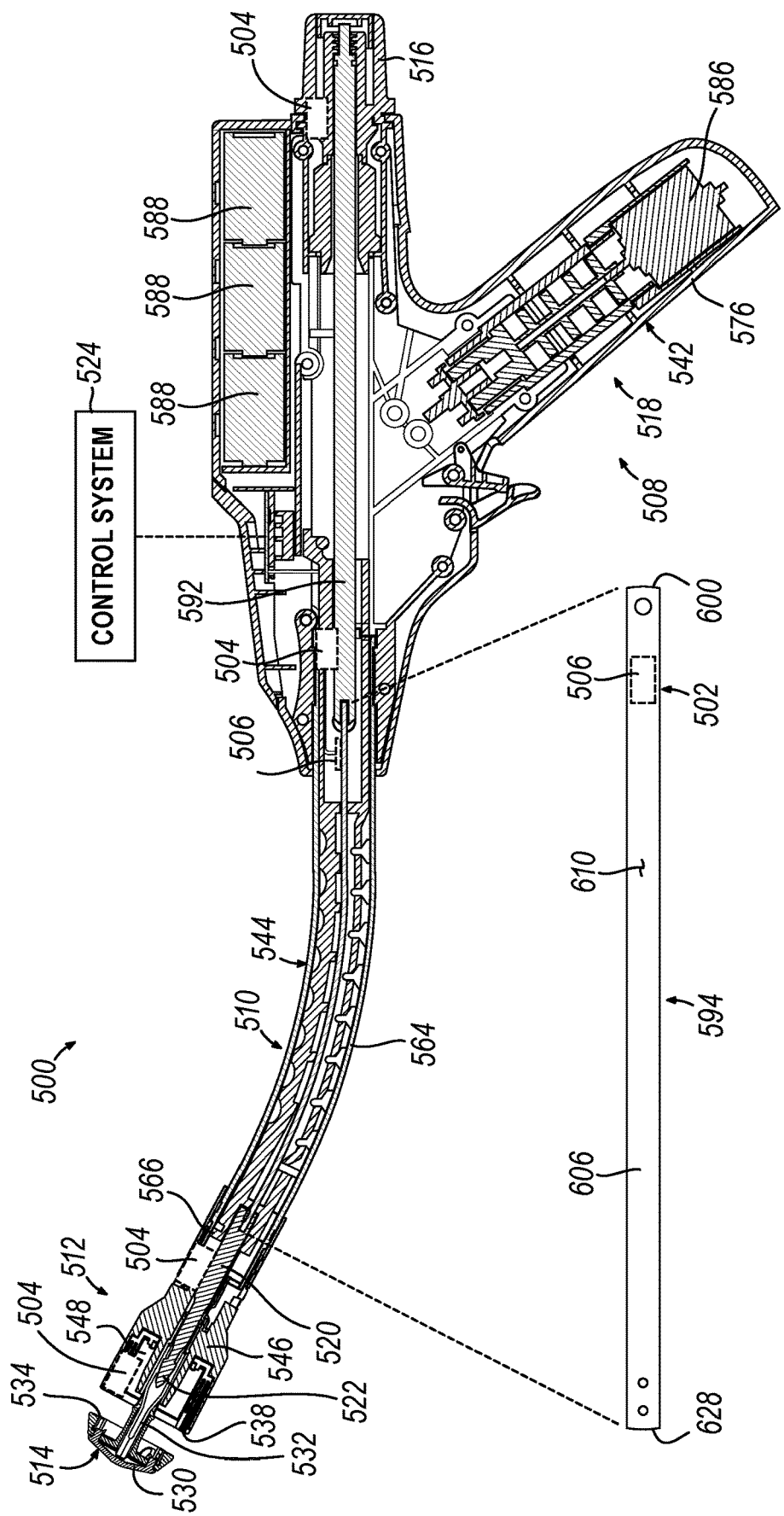
FIG. 8 depicts a cross-sectional view of another exemplary circular surgical stapler similar to the circular stapler of FIG. 1, but including a force sensor assembly.

FIGS. 8-15 show another exemplary circular surgical stapling instrument (500) that exhibits a configuration and functionality of the kind described above. It will be understood that instrument (500) is similar to instrument (10) described above except as otherwise described below. Particularly, FIG. 8 shows a sectional view of instrument (500) similar to instrument (10) of FIG. 1, but with instrument (500) additionally including a force sensing assembly (502).

Similar to instrument (10), instrument (500) includes a body assembly in the form of a handle assembly (508) (similar to handle assembly (100)), a shaft assembly (510) (similar to shaft assembly (200)), a stapling head assembly (512) (similar to stapling head assembly (300)), an anvil (514) (similar to anvil (400)), and an actuator in the form of a rotatable knob (516) (similar to knob (130). It is envisioned that the actuator may include other suitable alternatives, including a manually slidable lever or be electrically powered using motor (160) or another similar motor. These components are similar to respective components of the same name of instrument (10) described above with reference to FIGS. 1-7E. Similar to instrument (10), handle assembly (508) is configured to be gripped by a user, shaft assembly (510) extends distally from handle assembly (508), and stapling head assembly (512) is disposed at a distal end of shaft assembly (510).

As will be described in greater detail below, force sensing assembly (502) includes at least one compression force sensor (504) configured to sense a compression force experienced by instrument (500) and/or at least one tension force sensor (506) configured to sense a tension force experienced by instrument (500). For example, force sensing assembly (502) may include at least one compression force sensor (504), at least one tension force sensor (506), or at least one compression force sensor (504) and at least one tension force sensor (506). Instrument (500) may be considered as a system of compression and tension during tissue compression (i.e., clamping) and during firing of instrument (500). When anvil (514) clamps compressed tissue, components in instrument (500) experience at least one of tension or compression. During firing, the magnitude of these tension and compression forces in instrument (500) increases.

Figure 10:
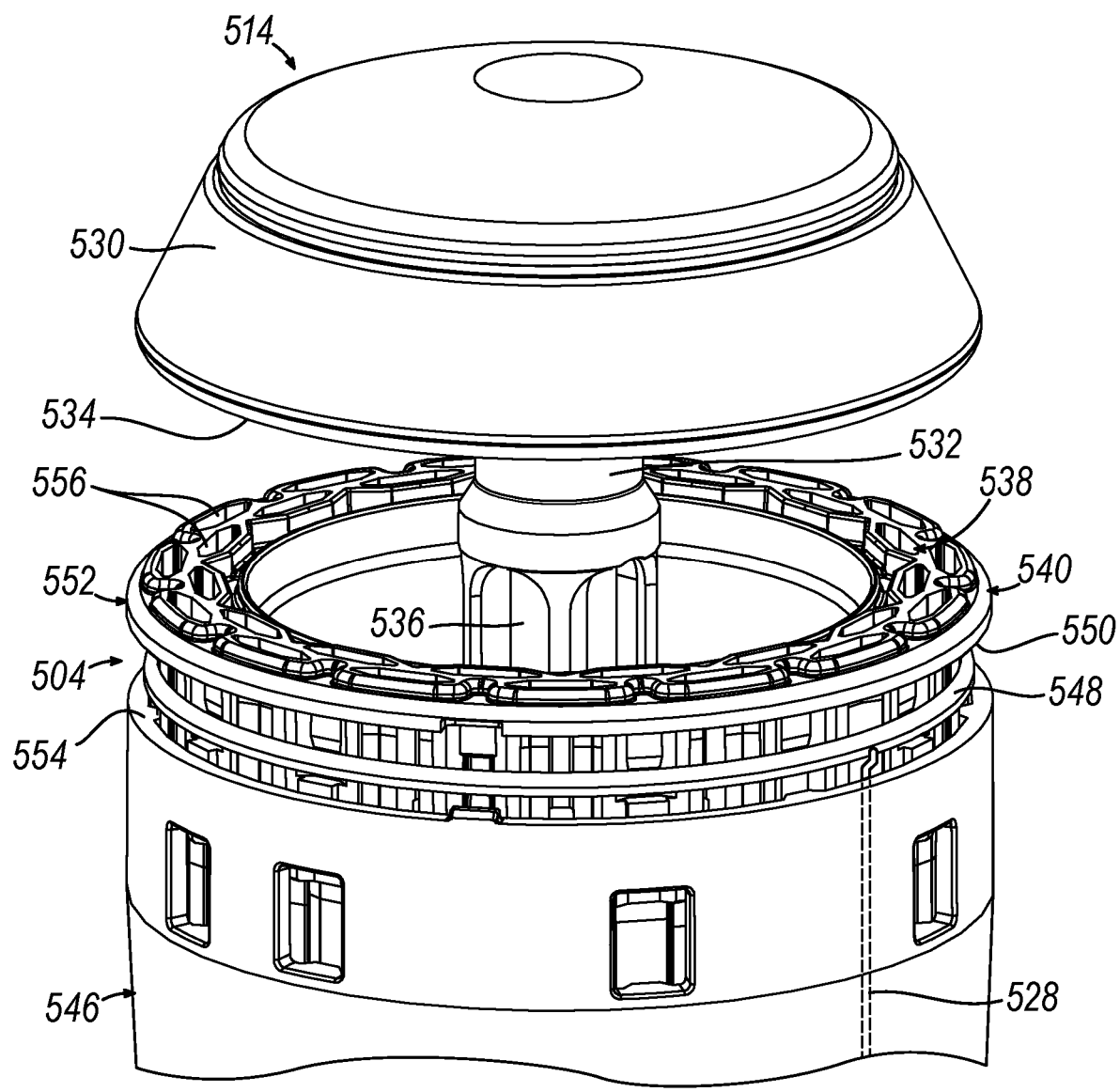
FIG. 10 depicts an enlarged perspective view of a distal end of the circular stapler of FIG. 8, with a compression force sensor disposed between a deck member and the casing of FIG. 9.

As will be described in greater detail below with reference to FIGS. 8-15, instrument (500) includes a housing assembly (518) and a movable member (520), where movable member (520) moves relative to housing assembly (518) using the actuator (e.g., knob (516)). Housing assembly (518) experiences a compression force and movable member (520) experiences a tension force when anvil (514) is coupled with a trocar (522) (similar to trocar (330)), and knob (130) is rotated by the user. The tension caused by the rotational input on knob (516) causes movable member (520) including trocar (522) to move proximally. In other words, applying a torque to close the gap (d) using rotatable knob (516) pulls movable member (520) proximally causing the compression and tension forces. As a result, stress and/or strain may be measured in instrument (500). As shown in FIG. 10, housing assembly (518) is collectively defined by adjacent housings of handle assembly (508), shaft assembly (510), stapling head assembly (512), and knob (516) that bear the compression force. As shown in FIG. 14, movable member (520) is collectively formed by portions of shaft assembly (510) and trocar (522) of stapling head assembly (512).

C. Exemplary Control System

Instrument (500) may include a control system (524) operable to control actuation of instrument (500). Control system (524) may include a user interface feature (526), a motor unit, and related circuitry that interfaces with force sensing assembly (502). Compression force sensor (504) and tension force sensor (506) may be electrically coupled with control system (524) using one or more wires (528). As described in greater detail with reference to FIG. 15, user interface feature (526) may indicate whether the sensed compression force and/or the sensed tension force is within an acceptable range. Control system (524) may include a processor, a memory, and a printed circuit board. Control system (524) may be disposed within instrument (500) or be disposed external to instrument (500) but in wired or wireless communication with instrument (500). Control system (524) may be operable to store pre-programmed instrument control algorithms and receive input from user interface feature (526) and force sensing assembly (502). Based on these stored control algorithms and received input, control system (524) is configured to determine tissue compression at the distal end of instrument (500).

This tissue compression data may be processed on an integrated printed circuit board (PCB) of instrument (500) and uploaded to cloud storage for subsequent data analytics. For example, average force to fire among other characteristics may be determined. While not shown, the printed circuit board (PCB) may be disposed in handle assembly (508) near user interface feature (526). For example, wires (528) may be routed to the PCB for resistance interpretation and correlation to compression force. In some versions, at least one of control system (524) or user interface feature (526) may be in signal communication with an external network, such that the compression force data may be directly uploaded to a cloud for data interpretation. For example, the teachings disclosed herein may be combined with any of the teachings of U.S. Pub. No. 2019/0201136, entitled "Method of Hub Communication," published Jul. 4, 2019; U.S. Pub. No. 2019/0206569, entitled "Method of Cloud Based Data Analytics for Use with the Hub," published Jul. 4, 2019; U.S. Pub. No. 2020/0100830, entitled "Method for Constructing and Using a Modular Energy System with Multiple Devices," published Apr. 2, 2020; and U.S. Prov. Pat. App. No. 63/018,664, entitled "Stabilizer for Surgical Shafts or Cannulas," filed on May 1, 2020, the disclosures of which are incorporated by reference herein. In some versions, the tissue compression data may be pushed to desired smart connected devices.

D. Exemplary Anvil

Anvil (514) is similar to anvil (400) described above with reference to FIG. 3. Anvil (514) is configured to be selectively coupled with movable member (520) to clamp, staple, and cut tissue using stapling head assembly (512). Anvil (514) and stapling head assembly (512) are configured to cooperate to manipulate tissue in three ways, including clamping the tissue, cutting the tissue, and stapling the tissue. Anvil (514) of the present example comprises a head (530) and a shank (532). Head (530) includes a proximal surface (534) that defines a plurality of staple forming pockets (not shown), which are similar to staple forming pockets (414). The staple forming pockets are configured to deform staples as the staples are driven into the staple forming pockets.

Particularly, anvil (514) selectively couples with trocar (522) using latch members (536), which are similar to latch members (430). Latch members (536) act as retaining clips to allow anvil (514) to be removably secured to an actuatable closure member in the form of a trocar (522). Anvil (514) is selectively retractable and extendable by trocar (522) relative to stapling head assembly (512) for clamping tissue against a distally facing deck surface (538) of a deck member (540) (similar to deck member (320)). When anvil (514) is coupled with trocar (522), rotation of knob (516) provides corresponding translation of anvil (514) relative to stapling head assembly (512).

E. Exemplary Compression Force Sensing

FIG. 9 shows a sectional view of housing assembly (518) of instrument (500) of FIG. 8. As shown, housing assembly (518) includes at least first and second housings and deck surface (538) of instrument (500). The first and second housings are disposed adjacent one another. In some versions, the first and second housings are prevented from translating relative to one another. For example, in some versions, the first and second housings may be fixably coupled together using a variety of suitable methods. As shown, force sensing assembly (502) includes at least one compression force sensor (504) disposed between the first and second housings of housing assembly (518). For example, the first and second housings may include actuator (shown as knob (516)), a casing (542) of handle assembly (508), deck member (540) (i.e., guide), outer sheath (544) (similar to outer sheath (210)), and a body member (546) (similar to body member (310)). Compression force sensor (504) is configured to sense a compression force communicated longitudinally through housing assembly (518) while compressing tissue between anvil (514) and deck surface (538) of deck member (540) (i.e., the pre-fire tissue compression force) and/or through the firing of instrument (500) (i.e., the force to fire). As used herein, the pre-fire tissue compression force is the force experienced by instrument (500) as tissue is approximated in preparation for firing, and the force to fire is the force experienced by instrument (500) through the firing sequence (e.g., cutting and stapling of the tissue). Compression force sensor (504) may include a pressure sensor. For example, the pressure sensor may include a load cell. Compression forces may be experienced between adjacent components (i.e., the first and second housings) of housing assembly (518). Compression force sensor (504) may be electrically coupled with control system (524) using one or more wires (528).

FIG. 10 shows an enlarged view of the distal end of instrument (500) of FIG. 8, with a compression force sensor (504) disposed between a deck member (540) and body member (546) of FIG. 9. As shown, compression force sensor (504) includes an annular ring (548) that surrounds at least a portion of deck member (540). While compression force sensor (504) is shown as annular ring (548) in FIG. 10, it is envisioned that compression force sensor (504) may take a variety of suitable forms, compression force sensor (504) may be non-annular. Compression force sensor (504) may sense the pre-fire tissue compression force between body member (546) and deck member (540). Annular ring (548) allows for pre-fire tissue compression to be measured between the deck member (540) and body member (546). As shown, deck member (540) is movable relative to body member (546), which is different than that described with reference to instrument (10). The loose fit of annular ring (548) may allow deck member (540) to selectively translate proximally and selectively apply pressure between a bottom surface (550) of a flange (552) of deck member (540) and a distal end (554) of body member (546). Deck member (540) is pushed toward body member (546) to calculate the force on tissue being compressed prior to firing. As shown, an embedded electrical connection (shown as wire (528)) may be disposed within body member (546) to electrically connect annular ring (548) with control system (524) (shown in FIG. 8). As shown, deck member (540) includes concentric annular arrays of staple openings (556) (similar to staple openings (324)). In some other versions, staple openings (556) may be arranged in three or more concentric annular arrays.

Figure 11:
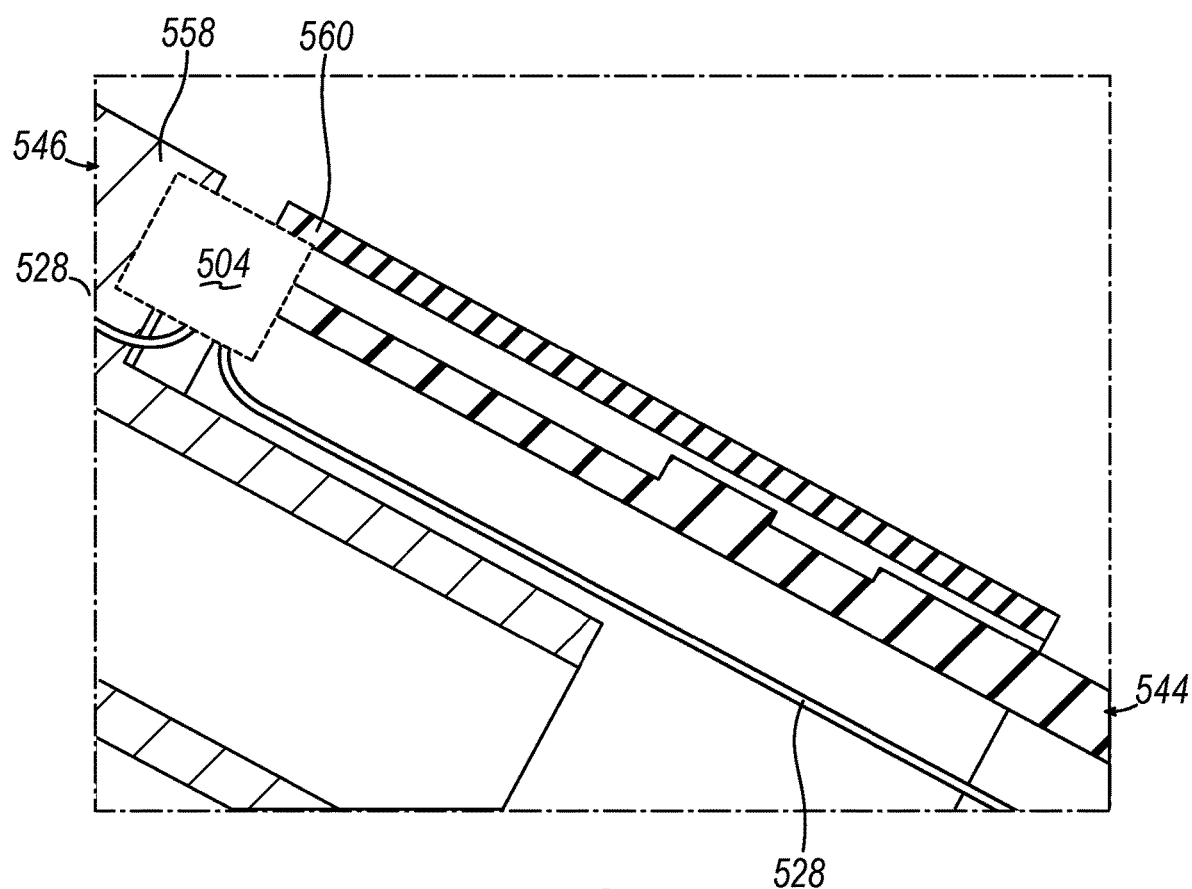
FIG. 11 depicts an enlarged detailed portion of the cross-sectional view of FIG. 9, schematically showing a compression force sensor disposed between the casing and the outer shaft.
Figure 12:
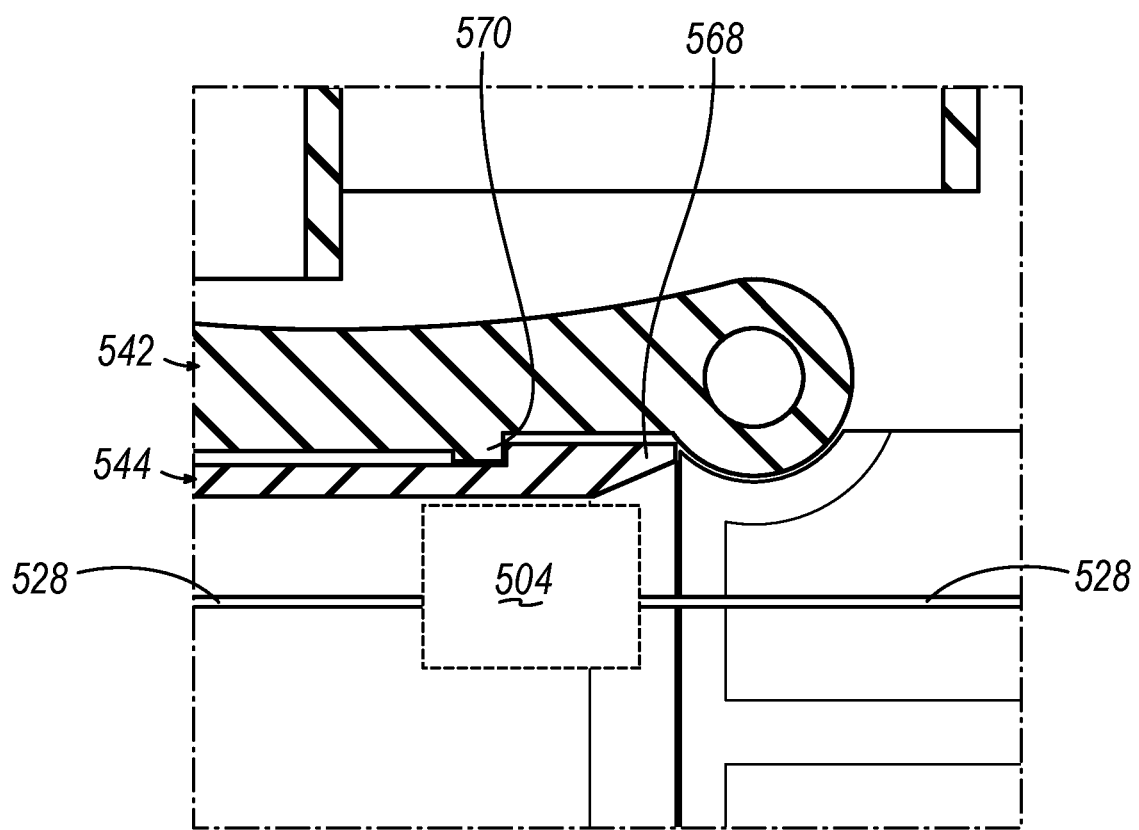
FIG. 12 depicts an enlarged detailed portion of the cross-sectional view of FIG. 9, schematically showing a compression force sensor disposed between the outer shaft and a casing of the handle assembly.
Figure 13:
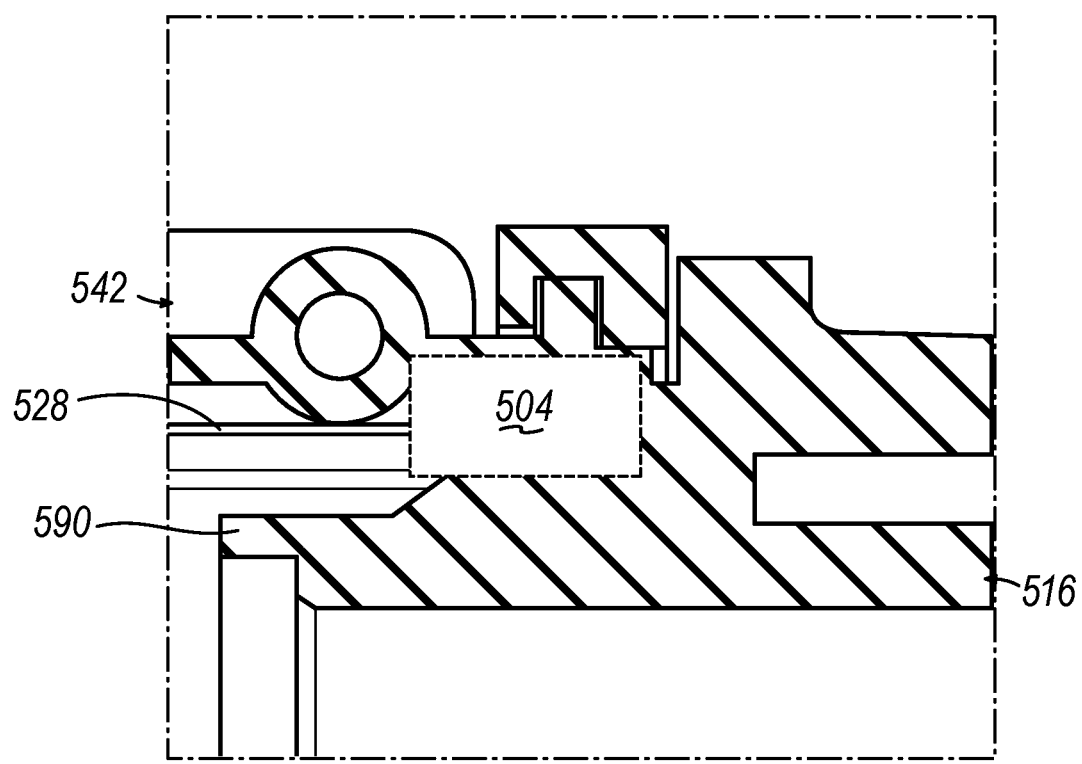
FIG. 13 depicts an enlarged detailed portion of the cross-sectional view of FIG. 9, schematically showing a compression force sensor disposed between the casing of the handle assembly and a knob.
Figure 14:
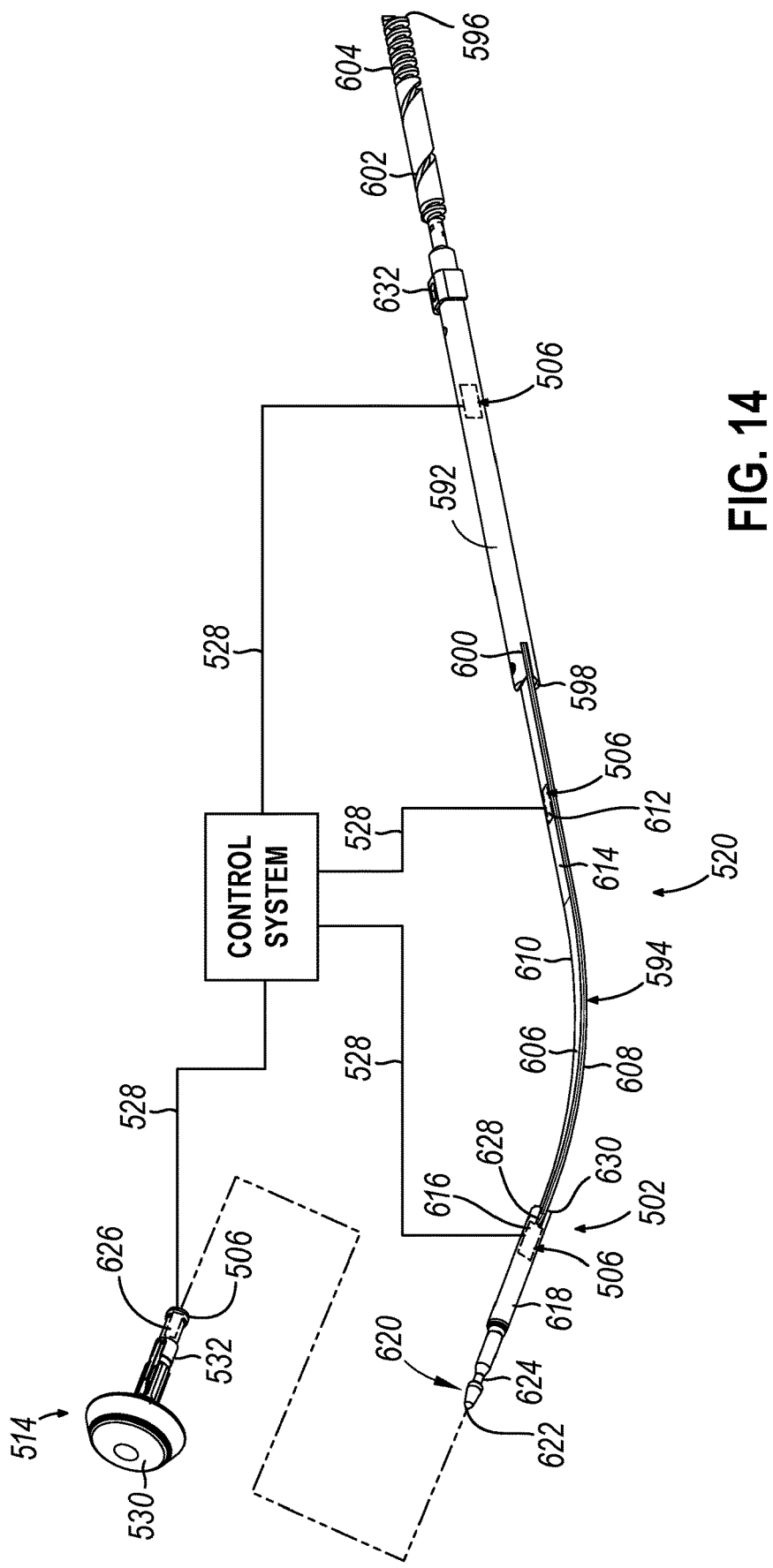
FIG. 14 depicts a perspective view of the movable member and anvil of FIG. 8 in combination with a control system, with the movable member including at least one tensile force sensor.

FIGS. 11-13 show representative positions of compression force sensor (504) disposed between first and second housings of housing assembly (518). While FIGS. 11-13 show representative positions of compression force sensor (504), other suitable positions and placement of compression force sensor (504) are also envisioned. The first and second housings may be coupled together at coupling points, which experience compression forces during pre-firing tissue compression and during firing of instrument (500). As a result, it may be beneficial to include one or more compression force sensors (504) may be disposed at these coupling points. For example, compression force sensor (504) disposed between body member (546) and outer sheath (544). In each of FIGS. 11-13, compression force sensor (504) may include a load cell.

FIG. 11 depicts a detailed portion of FIG. 9, where compression force sensor (504) is disposed between proximal end (558) of outer sheath (544) and a distal end (560) of body member (546). Compression force sensor (504) may be electrically coupled with control system (524) using one or more wires (528). Compression force sensor (504) may sense the pre-fire tissue compression force between outer sheath (544) and body member (546). Body member (546) is configured to surround at least a portion of movable member (520). Body member (546) includes a distally extending cylindraceous inner core member (562) (similar to inner core member (312)). Body member (546) is fixedly secured to an outer sheath (544) of shaft assembly (510). Body member (546) and outer sheath (544) together serve as a mechanical ground for stapling head assembly (512). Outer sheath (544) is configured to surround at least a portion of movable member (520). Outer sheath (544) is fixed relative to body member (546). Outer sheath (544) extends between handle assembly (508) and body member (546). In the present example, outer sheath (544) is rigid and includes a preformed curved section (564) (shown in FIGS. 8-9). Instrument (500) also includes a ferrule (566) that surrounds at least a portion of outer sheath (544), for example as disclosed in U.S. patent application Ser. No. 16/887,182, entitled "Shaft Attachment Feature for Circular Surgical Stapler," filed on May 29, 2020, the disclosure of which is incorporated by reference herein.

FIG. 12 depicts a detailed portion of FIG. 9, showing a compression force sensor (504) disposed between a proximal end (568) of outer sheath (544) and an internal mating feature (570) of casing (542) of handle assembly (508). Compression force sensor (504) may sense the pre-fire tissue compression force between proximal end (568) of outer sheath (544) and internal mating feature (570) of casing (542). Handle assembly (508) includes a casing (542). As shown in FIG. 9, casing (542) includes proximal and distal ends (572, 574). Casing (542) also includes an obliquely oriented pistol grip (576), with user interface feature (526) being disposed on an upper portion (578) of casing (542) adjacent to distal end (574) of casing (542). Knob (516) is rotatably disposed at proximal end (572) of casing (542). Handle assembly (508) includes several features that are operable to actuate anvil (514) and stapling head assembly (512). Similar to handle assembly (100), handle assembly (508) also includes a safety trigger (582), a firing trigger (584), a motor (586), and a motor activation module (not shown). Handle assembly (508) also includes a removable battery pack (588) operable to provide electrical power to a motor (similar to (160)) housed within handle assembly (508). Firing trigger (150) is configured to activate motor (160) to thereby actuate stapling head assembly (512). Safety trigger (140) is configured to selectively block actuation of firing trigger (150) based on the longitudinal position of anvil (514) in relation to stapling head assembly (512). As shown in FIG. 9, casing (542) of the present example includes an open-ended proximal cavity (580) configured to releasably receive and retain a battery pack (588) and operable to power motor (586) housed within casing (542).

FIG. 13 depicts a detailed portion of FIG. 9, showing a compression force sensor (504) disposed between casing (542) of handle assembly (508) and knob (516). Particularly, compression force sensor (504) is disposed between a proximal end (572) of casing (542) and a distal end (590) of knob (516). Compression force sensor (504) may sense the pre-fire tissue compression force between the actuator (e.g., knob (516)) and casing (542) of handle assembly (508) and/or the force to fire between the actuator (e.g., knob (516)) and casing (542) of handle assembly (508). Compression force sensor (504) may sense a compression force both during pre-fire tissue compression and during the firing sequence. Compression force sensor (504) may be electrically coupled with control system (524) using one or more wires (528). As described above, knob (516) is configured to translate movable member (520) including trocar (522) proximally and distally. Knob (516) may be rotated in a first angular direction (e.g., clockwise) to retract anvil (514) toward stapling head assembly (512); and in a second angular direction (e.g., counterclockwise) to advance anvil (514) away from stapling head assembly (512). Knob (516) may be used to adjust a gap distance (d) between proximal surface (534) of anvil (514) and deck surface (538) of deck member (540) until a suitable gap distance (d) has been achieved, as shown in FIG. 7C regarding instrument (10). Tension caused by rotational input on the knob (516) causes the trocar (522) to move proximally. Knob (516) is rotatable relative to casing (542) to provide precise clamping of the tissue between anvil (514) and deck member (540).

F. Tension Force Sensing

FIG. 14 shows a perspective view of movable member (520) of FIG. 8. Movable member (520) is configured to be actuated at least between an open position for receiving at least first and second layers of tissue and a closed position where at least first and second layers of tissue are compressed together. Movable member (520) may be at least partially disposed within housing assembly (518). As previously described, movable member (520) is collectively formed by portions of shaft assembly (510) as well as trocar (522) of stapling head assembly (512). As shown, movable member (520) includes trocar (522), a trocar actuation rod (592), and a trocar actuation connecting assembly (shown as a trocar actuation band assembly (594)). At least one tension force sensor (506) may be coupled with trocar actuation rod (592), trocar actuation band assembly (594), and/or trocar (522) to sense the tension force in trocar actuation rod (592), trocar actuation band assembly (594), and/or trocar (522). Tension force sensor (506) is configured to sense a tension force communicated longitudinally through movable member (520) and/or trocar (522) while compressing tissue between anvil (514) and deck surface (538) and/or firing instrument (500). Tension force sensor (506) may sense a tension force during pre-fire tissue compression and during the firing sequence.

Trocar actuation rod (592) has proximal and distal ends (596, 598), such that a proximal end (600) of trocar actuation band assembly (594) is fixed relative to distal end (598) of trocar actuation rod (592). A proximal end (596) of trocar actuation rod (592) is coupled with knob (516). Trocar actuation rod (592) includes a coarse helical threading (602) and a fine helical threading (604). Knob (516) is coupled with trocar actuation rod (592) via a nut (not shown), such that coarse helical threading (602) selectively engages a thread engagement feature within the interior of the nut, and fine helical threading (226) selectively engages a thread engagement feature within the interior of knob (516). As shown, tension force sensor (506) may be coupled with trocar actuation rod (592), such that tension force sensor (506) may be electrically coupled with control system (524) using one or more wires (528).

Tension force sensor (506) may be coupled with trocar actuation band assembly (594). Trocar actuation band assembly (594) may include multiple tension bands, which are shown as being stacked together. As shown in FIG. 14, trocar actuation band assembly (594) includes upper and lower tension bands (606, 608). In some versions, upper and lower tension bands (606, 608) may be formed from a metallic material, such that one of upper and lower tension bands (606, 608) in instrument (500) that retract anvil (514) against tissue is under tension during tissue compression and firing where knife pushes on anvil (514). Tension force sensor (506) may be fixably coupled with one of upper and lower tension bands (606, 608).

As shown, tension force sensor (506) is fixably coupled with an upper surface (610) of upper tension band (606). Tension force sensor (506) may include a strain gage (612). For example, strain gage (612) may be positioned on a planar portion (614) of upper tension band (606) of trocar actuation band assembly (594), which undergoes tension during tissue compression. Upper tension band (606) experiences higher tension when firing instrument (500), this increase in strain may be sensed by strain gage (612) and transmitted to control system (524) using one or more wires (528). As a result of the sensed strain, control system (524) may then correlate the strain to a pre-fire tissue compression force and/or a force to fire at the distal end of instrument (500). Tension force sensor (506) may be embedded on upper surface (610) and measure the surface strain and back calculate the pre-fire tissue compression force and/or the force to fire at the distal end of instrument (500). Alternatively, strain gage (612) may include an in-line strain gage. The in-line strain gage may be placed between respective components of movable member (520). For example, an in-line strain gage may be placed where two components mate. In some versions, a portion of movable member (520) (e.g., a portion of trocar actuation band assembly (594) or a portion of trocar actuation rod (592)) may be removed and replaced with an in-line strain gage. Trocar (522) is described below with reference to an in-line strain gage (616).

As shown in FIG. 14, the pre-fire tissue compression force and/or the force to fire may be measured using tension force sensor (506) disposed coupled with the trocar (522), such that tension force sensor (506) may be electrically coupled with control system (524) using one or more wires (528). Trocar (522) is operable to translate distally and proximally relative to body member (546) in response to rotation of knob (516) relative to casing (542) of handle assembly (508). Trocar (522) comprises a shaft (618) and a head (620). Head (620) includes a pointed tip (622) and an inwardly extending proximal surface (624). Head (620) and the distal portion of shaft (618) are configured for insertion in a bore (not shown but similar to bore (422) of anvil (400)). Anvil (514) is thus secured to trocar (522) through a snap fit provided by latch members (536). Latch members (536) of anvil (514) capture trocar (522) causing tension on intermediate components of movable member (520) (e.g., trocar actuation rod (592), trocar actuation band assembly (594)). The pre-fire tissue compression force and/or the force to fire may be measured using a strain gage (626) on shaft (618) of anvil (514).

As shown in FIG. 14, distal end (628) of trocar actuation band assembly (594) is fixedly secured to a proximal end (630) of shaft (618) of trocar (522). It should therefore be understood that trocar (522) will translate longitudinally relative to outer sheath (544) in response to translation of trocar actuation band assembly (594) and trocar actuation rod (592) relative to outer sheath (544). Trocar actuation band assembly (594) is configured to flex such that trocar actuation band assembly (594) may follow along the preformed curve in shaft assembly (510) as trocar actuation band assembly (594) is translated longitudinally relative to outer sheath (544). However, trocar actuation band assembly (594) has sufficient column strength and tension strength to transfer distal and proximal forces from trocar actuation rod (592) to shaft (618) of trocar (522). Trocar actuation rod (592) is rigid. A clip (632) is fixedly secured to trocar actuation rod (592) and is configured to cooperate with complementary features within handle assembly (508) to prevent trocar actuation rod (592) from rotating within handle assembly (508) while still permitting trocar actuation rod (592) to translate longitudinally within handle assembly (508).

Similar to stapling head assembly (300), stapling head assembly (512) includes a deck member (540) and a trocar (522). Stapling head assembly (512) is selectively operable to eject staples distally into the clamped tissue and against anvil (514), and to cut the clamped tissue with a cylindraceous knife member (not shown) similar to knife member (340) described above. Accordingly, stapling head assembly (512) and anvil (514) cooperate to define an end effector stapling assembly operable to clamp, staple, and cut tissue in response to user inputs.

Instrument (500) may be further configured and operable in accordance with at least some of the teachings of U.S. Pat. No. 9,445,816, entitled "Circular Stapler with Selectable Motorized and Manual Control," issued Sep. 20, 2016; U.S. Pat. No. 9,532,783, entitled "Circular Stapler with Select Motorized and Manual Control, Including a Control Ring," issued Jan. 3, 2017; U.S. Pat. No. 9,597,081, entitled "Motor Driven Rotary Input Circular Stapler with Modular End Effector," issued Mar. 21, 2017; U.S. Pat. No. 9,463,022, entitled "Motor Driven Rotary Input Circular Stapler with Lockable Flexible Shaft," issued Oct. 11, 2016; U.S. Pub. No. 2018/0368836, entitled "Surgical Stapler with Independently Actuated Drivers to Provide Varying Staple Heights," published Dec. 27, 2018; and/or any of the other patent references identified herein, the disclosures of which are incorporated by reference herein.

G. Exemplary Manually Actuated Circular Stapler

While not shown, force sensing assembly (502) may be incorporated into a manually actuated circular stapler, instead of instrument (500), which is shown as a powered circular stapler. For example, force sensing assembly (502) may be applied to a manually actuated circular stapler, such as the kind described in U.S. Pat. Pub. No. 2020/0113565, entitled "Latch to Prevent Back-Driving of Circular Surgical Stapler," published Apr. 16, 2020, the disclosure of which is incorporated by reference herein. A power source (not shown) may be included to power force sensing assembly (502) for the manually actuated circular stapler. For example, the power source may be electrically coupled with a strain gage.

H. Exemplary User Interface Feature of Handle Assembly

Figure 15:
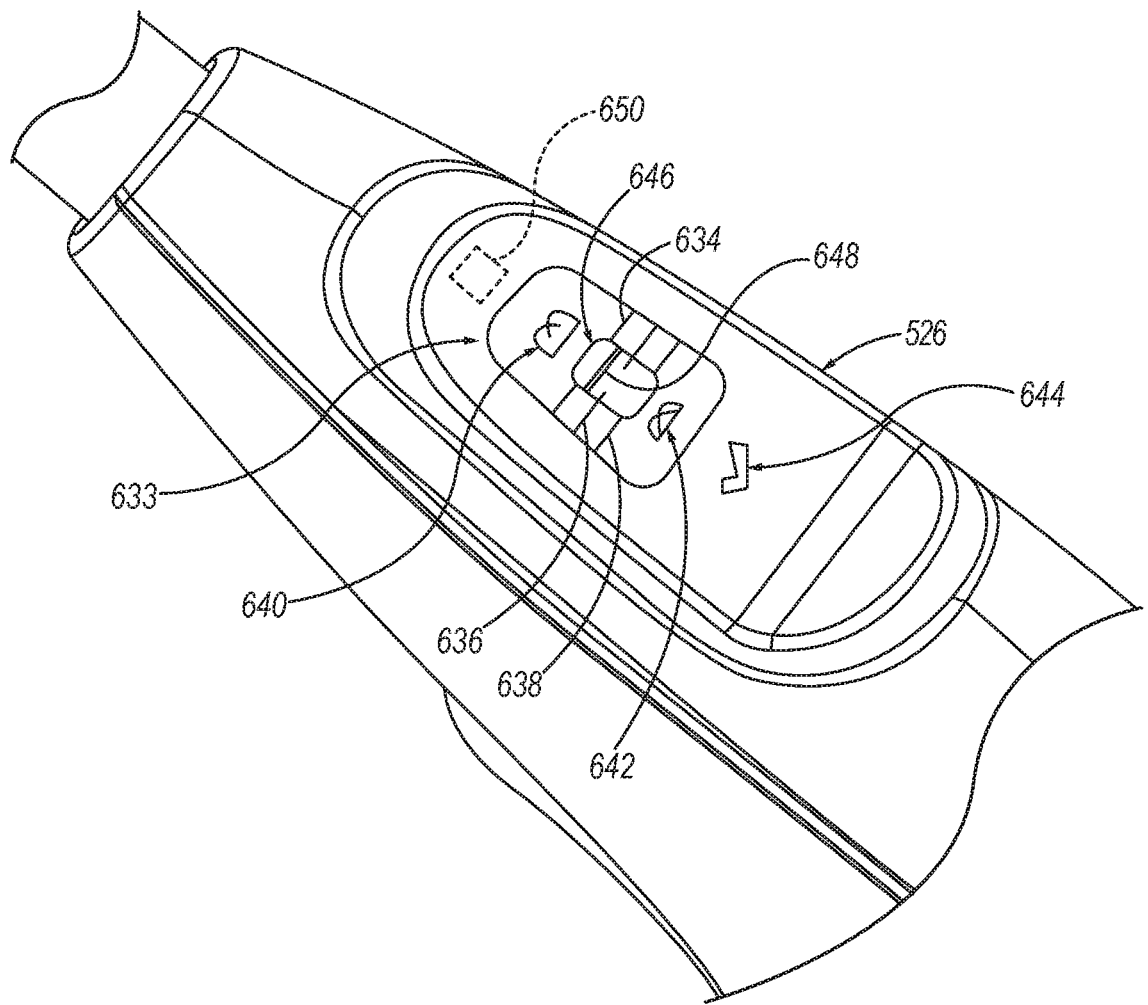
FIG. 15 depicts a perspective view of a user interface feature of the handle assembly of the circular stapler of FIG. 8.

FIG. 15 shows a perspective view of a user interface feature (526) of handle assembly (508) of instrument (500) of FIG. 8. User interface feature (114) configured to provide the operator with visual feedback indicating the positioning of anvil (514) in relation to stapling head assembly (512) during a surgical procedure. The operator may observe user interface feature (526) while rotating knob (516) to confirm whether a suitable gap distance (d) between anvil (514) and stapling head assembly (512) has been achieved. User interface feature (526) of the present example includes a graphical indicator (633), which includes fixed linear indicia (634, 636, 638), graphical representations (640, 642) of staples, and a checkmark graphic (644). User interface feature (114) further defines a window (646) through which an indicator needle (648) may be viewed. Circular surgical stapling instrument (500) may be further configured and operable in accordance with at least some of the teachings of U.S. Pat. No. 10,709,452, issued on Jul. 14, 2020, incorporated by reference above.

User interface feature (526) is configured to receive and communicate user input to control system (524). In that regard, user interface feature (526) may include one or more buttons, dials, other actuatable elements, or displayed graphics that are selectable by a user to indicate certain information pertaining to a surgical procedure to be performed or to stapling head assembly (512). By way of example only, such information may include any of the following: a desired staple formation height; a corresponding gap between anvil (514) and stapling head assembly (512) to which anvil (514) should be actuated during closure; a type or nominal thickness of tissue being fired upon with instrument (500); and/or a diameter of stapling head assembly (512). As the operator rotates knob (516) to adjust the longitudinal position of anvil (514) relative to stapling head assembly (512), the operator may observe the tissue compression force being actively sensed by instrument (500).

This information may be provided to the surgeon on a real time display (variable or attribute) to ensure tissue compression is uniform. In some versions, user interface feature (526) may display the compression force for the user. For example, user interface feature (526) may include a tissue compression screen (650). The user may be informed of the pre-fire tissue compression force using an LED panel. The pre-fire compression force may be presented as a discrete pass/fail signal (e.g., colored indictors such as green and red lights) or a quantitative readout. For example, the strain data may be processed to determine the pre-fire tissue compression force and/or force to fire during the firing stroke at the distal end of instrument (500). Alternatively, or in addition to user interface feature (526), instrument (500) may be in signal communication with an external network, such that the pre-fire tissue compression force and/or the force to fire may be directly uploaded to a cloud for data interpretation to determine the correlated pre-fire tissue compression force and/or force to fire during the firing stroke at the distal end of instrument (500). Additionally, the pre-fire tissue compression force and/or force to fire data may be recorded for real time field monitoring and to prevent trends. Compression force may be obtained from strain gage and a correlation may be formulated to determine tissue compression and force to fire tension values that correspond to pre-fire tissue compression and/or force to fire at the distal end of instrument (500).

I. Exemplary Method

Figure 16:
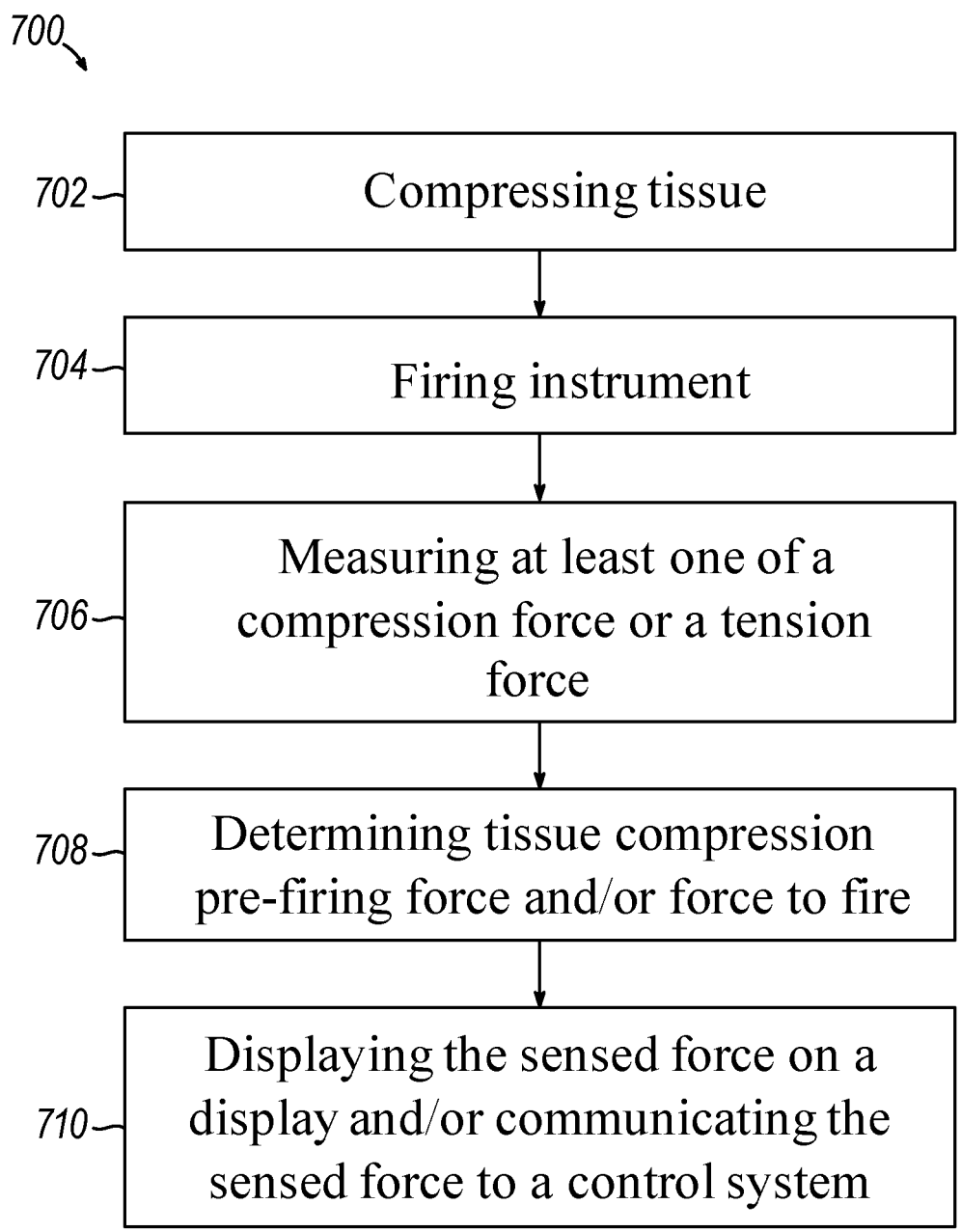
FIG. 16 depicts a diagrammatic view of an exemplary method of operating the circular stapler of FIG. 8.

An exemplary method (700) of measuring tissue compression of instrument (500) is described below with reference to FIG. 16. At step (702), the method (700) may include compressing tissue between anvil (514) and the deck surface (538). At step (704), the method (700) may include firing instrument (500) to drive staples through the tissue. At step (706), the method (700) may include measuring at least one of the compression force communicated longitudinally through housing assembly (518) between the first and second housings and/or the tension force communicated longitudinally through movable member (520) or anvil (514). As described above, the compression force communicated longitudinally through housing assembly (518) while compressing tissue between anvil (514) and deck surface (538) or while firing instrument (500) may be measured using a compression force sensor (504) disposed between the first and second housings.

For example, the pre-fire tissue compression force may be measured using at least one compression force sensor (504) positioned at one or more of following positions between deck member (540) and body member (546) (i.e., casing), between body member and outer sheath (544), between outer sheath (544) and casing (542) of handle assembly (508), and between casing (542) of handle assembly (508) and knob (516). The force to fire may be measured using at least one compression force sensor (504) positioned between casing (542) of handle assembly (508) and knob (516). As described above, the tension force communicated longitudinally through movable member (520) while compressing tissue between anvil (514) and deck surface (538) or firing instrument (500) may be measured using a tension force sensor (506) coupled with movable member (520). For example, at least one tension force sensor (506) may be coupled with trocar actuation rod (592), trocar actuation band assembly (594), and/or trocar (522) to sense the tension force in trocar actuation rod (592), trocar actuation band assembly (594), and/or trocar (522).

At step (708), the method (700) may include determining at least one force based on the sensed compression force obtained from compression force sensor (504) and/or the sensed tension force obtained from tension force sensor (506). For example, the force with which instrument (500) compresses tissue disposed between deck surface (538) and anvil (514) at a time prior to firing of instrument (500) and/or the force with which a firing assembly of instrument (500) is actuated to fire instrument (500) on the compressed tissue may be determined. Determining the tissue compression force may include correlating measurement of the compression force and/or the tension force to the amount of tissue compression prior to firing of instrument (500) or during firing of instrument (500) using an algorithm. The algorithm may be determined based on the sensed data of other firings. The algorithm may include a transfer function that measures the actual compression force with a calibrated system, then correlates the corresponding strain and compression from inside instrument (500) at the various locations. For example, a lookup table may be used.

After determining the tissue compression force, at step (710), the method (700) may include communicating the sensed force to user interface feature (526) and/or communicating the sensed force to control system (524). Communicating the sensed force may include producing an indication that the tissue compression is within an acceptable range. For example, the indication may include one or more of an audible, tactile, or visual indication. Instrument (500) may provide feedback to user or algorithm to ensure optimal compression. Instrument (500) may also collect data for post-processing related to performance of instrument (500). For example, instrument (500) may record data pertaining to tissue compression prior to firing and tissue compression during firing. After determining tissue compression, the method may also include uploading tissue compression data to a cloud as described above.

Instrument (500) may provide multiple benefits including measuring and determining the force of pre-fire tissue compression force and/or the force to fire instrument (10) using actual data from instrument (10). In some versions, instrument (500) may obtain real time data thereby allowing the user to take actions to improve staple formation, and obtain data from multiple instruments to ascertain trends for the desired alterations. In some versions, instrument (500) may allow for measurement of actual pre-fire tissue compression force and/or the force to fire without routing one or more wires through at least portions of shaft assembly (510) and stapling head assembly (512) using the algorithm.

III. Exemplary Combinations

The following examples relate to various non-exhaustive ways in which the teachings herein may be combined or applied. The following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument comprising: (a) a housing assembly comprising: (i) a first housing, (ii) a second housing disposed adjacent the first housing, and (iii) a deck surface that includes at least one annular array of staple openings; (b) a movable member at least partially disposed within the housing assembly; (c) an anvil configured to be selectively coupled with the movable member to compress tissue between the anvil and the deck surface; and (d) a force sensing assembly, wherein the force sensing assembly comprises at least one of: (i) a compression force sensor disposed between the first and second housings, wherein the compression force sensor is configured to sense a compression force communicated longitudinally through the first and second housings during at least one of compressing the tissue between the anvil and the deck surface or firing the surgical instrument, or (ii) a tension force sensor coupled with the movable member or the anvil, wherein the tension force sensor is configured to sense a tension force communicated longitudinally through the movable member during at least one of compressing the tissue between the anvil and the deck surface or firing the surgical instrument.

Example 2

The surgical instrument of Example 1, wherein the force sensing assembly comprises the compression force sensor disposed between the first and second housings.

Example 3

The surgical instrument of any of the preceding Examples, wherein the compression force sensor includes a load cell.

Example 4

The surgical instrument of any of the preceding Examples, wherein the first housing includes a body member configured to surround at least a portion of the movable member, wherein the second housing includes a deck member, wherein the deck member includes the deck surface, wherein the compression force sensor is configured to sense the compression force between the body member and the deck member during compressing the tissue between the anvil and the deck surface.

Example 5

The surgical instrument of Example 4, wherein the compression force sensor includes an annular ring that surrounds at least a portion of the deck member during compressing the tissue between the anvil and the deck surface.

Example 6

The surgical instrument of any one or more of Examples 1 through 3, wherein the first housing includes an outer sheath configured to surround at least a portion of the movable member, wherein the second housing includes a body member configured to surround at least a portion of the movable member, wherein the outer sheath is fixed relative to the body member, wherein the compression force sensor is configured to sense the compression force between the outer sheath and the body member during compressing the tissue between the anvil and the deck surface.

Example 7

The surgical instrument of any one or more of Examples 1 through 3, wherein the first housing includes a handle assembly configured to be gripped by a user, wherein the second housing includes an outer sheath configured to surround at least a portion of the movable member, wherein the handle assembly is fixed relative to the outer sheath, wherein the compression force sensor is configured to sense the compression force between the handle assembly and the outer sheath during compressing the tissue between the anvil and the deck surface.

Example 8

The surgical instrument of any one or more of Examples 1 through 3, wherein the first housing includes an actuator configured to translate the movable member, wherein the second housing includes a handle assembly configured to be gripped by a user, wherein the compression force sensor is configured to sense the compression force between the actuator and the handle assembly during at least one of compressing the tissue between the anvil and the deck surface or firing the surgical instrument.

Example 9

The surgical instrument of any of the preceding Examples, wherein the anvil includes a head and a shaft, wherein the shaft is configured to be selectively coupled with the movable member to compress tissue between the anvil and the deck surface, wherein the tension force sensor is coupled with the movable member or the shaft of the anvil.

Example 10

The surgical instrument of any of the preceding Examples, wherein the movable member includes a trocar actuation connecting assembly, wherein the tension force sensor is fixably coupled with the trocar actuation connecting assembly.

Example 11

The surgical instrument of Example 10, wherein the trocar actuation connecting assembly includes upper and lower tension bands, wherein the tension force sensor is fixably coupled with the upper tension band.

Example 12

The surgical instrument of any of the preceding Examples, wherein the tension force sensor includes an in-line strain gage.

Example 13

The surgical instrument of any one or more of Examples 1 through 9 and Example 12, wherein the movable member includes a trocar actuation band assembly and a trocar, wherein the trocar is translatably coupled with the trocar actuation band assembly, wherein the tension force sensor is disposed on the trocar actuation band assembly, the trocar, or between the trocar actuation band assembly and the trocar.

Example 14

The surgical instrument of any of the preceding Examples, further comprising a control system, wherein the force sensing assembly includes a wire that electrically connects at least one of the tension force sensor or the compression force sensor with the control system.

Example 15

The surgical instrument of Example 14, wherein the control system includes a user display feature, wherein the control system is electrically coupled with the user display feature, wherein the user display feature is configured to at least one of display the compression or tension force, display whether the compression or tension force is within an acceptable range, record the compression or tension force, or the upload the compression or tension force to a cloud.

Example 16

A surgical instrument comprising: (a) a handle assembly, wherein the handle assembly includes a casing; (b) a shaft assembly extending distally from the handle assembly, wherein the shaft assembly includes an outer sheath, a trocar actuation rod, and a trocar actuation connecting assembly; (c) a stapling head assembly extending distally from the shaft assembly, wherein the stapling head assembly comprises: (i) a body member, (ii) a deck member that includes an annular array of staple openings, and (iii) a trocar; (d) an anvil that includes a head and a shaft, wherein the shaft is configured to be selectively coupled with the trocar to compress tissue; (e) an actuator that is configured to translate the trocar relative to the handle assembly; and (f) a force sensing assembly, wherein the force sensing assembly comprises: (i) a compression force sensor configured to sense compression force communicated longitudinally through the surgical instrument, wherein the compression force sensor is positioned between: (1) the deck member and the body member, (2) the body member and the outer sheath, (3) the outer sheath and the casing, or (4) the casing and the actuator, or (ii) a tension force sensor coupled with at least one of the trocar actuation rod, the trocar actuation connecting assembly, the trocar, or the shaft of the anvil, wherein the tension force sensor is configured to sense tension force communicated longitudinally through the shaft assembly, the trocar, or the anvil.

Example 17

A method of using a surgical instrument, the surgical instrument comprising a housing assembly comprising first and second housings that are disposed adjacent one another, and a deck surface that includes at least one annular array of staple openings, a movable member at least partially disposed within the housing assembly, an anvil configured to be selectively coupled with the movable member, and at least one of a compression force sensor or a tension force sensor, the method comprising: (a) compressing tissue between the anvil and the deck surface; (b) firing the surgical instrument to drive staples through the tissue; (c) measuring at least one of: (i) a compression force communicated longitudinally through the housing assembly between the first and second housings while at least one of compressing tissue between the anvil and the deck surface or firing the surgical instrument, using a compression force sensor disposed between the first and second housings, or (ii) a tension force communicated longitudinally through the movable member while at least one of compressing the tissue between the anvil and the deck surface or firing the surgical instrument, using a tension force sensor coupled with the movable member; and (d) based on at least one of the compression force or the tension force, determining at least one of: (i) a force with which the surgical instrument compresses tissue disposed between the deck surface and the anvil at a time prior to firing of the surgical instrument, or (ii) a force with which a firing assembly of the surgical instrument is actuated to fire the surgical instrument on the compressed tissue.

Example 18

The method of Example 17, further comprising, after determining the tissue compression, producing an indication that tissue compression is within an acceptable range.

Example 19

The method of any one or more of Examples 17 through 18, wherein the step of measuring further comprises correlating the measurement of the compression force or the tension force to an amount of tissue compression prior to firing of the surgical instrument or during firing of the surgical instrument using an algorithm.

Example 20

The method of any one or more of Examples 17 through 19, further comprising, after determining at least one of the forces, uploading the at least one of the forces to a cloud.

IV. Miscellaneous

It should also be understood that any one or more of the teachings, expressions, embodiments, examples, etc. described herein may be combined with any one or more of the other teachings, expressions, embodiments, examples, etc. that are described herein.

The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

The teachings disclosed herein may be combined with any of the teachings of U.S. patent application Ser. No. 16/925,448, entitled "Load Sensor for Circular Surgical Stapler," filed on Jul. 10, 2020, issued as U.S. Pat. No. 11,490,891 on Nov. 8, 2022, the disclosure of which is incorporated by reference herein.

Furthermore, any one or more of the teachings herein may be combined with any one or more of the teachings disclosed in U.S. patent application Ser. No. 16/574,797, entitled "Method for Controlling Cutting Member Actuation for Powered Surgical Stapler," filed on Sep. 18, 2019, issued as U.S. Pat. No. 11,123,074 on Sep. 21, 2021; U.S. patent application Ser. No. 16/574,281, entitled "Method for Controlling End Effector Closure for Powered Surgical Stapler," filed on Sep. 18, 2019, issued as U.S. Pat. No. 11,185,331 on Nov. 30, 2021; and U.S. patent application Ser. No. 16/574,299, entitled "Anvil Retention and Release Features for Powered Circular Surgical Stapler," filed on Sep. 18, 2019, issued as U.S. Pat. No. 11,185,324 on Nov. 30, 2021. The disclosure of each of these U.S. patent applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument comprising:
   (a) a housing assembly comprising:
      (i) a first housing,
      (ii) a second housing disposed adjacent the first housing, and
      (iii) a deck surface that includes at least one annular array of staple openings;
   (b) a movable member at least partially disposed within the housing assembly;
   (c) an anvil configured to be selectively coupled with the movable member to compress tissue between the anvil and the deck surface; and
   (d) a force sensing assembly, wherein the force sensing assembly comprises at least one of:
      (i) a compression force sensor disposed between the first and second housings, wherein the compression force sensor is configured to sense a compression force communicated longitudinally through the first and second housings during at least one of compressing the tissue between the anvil and the deck surface or firing the surgical instrument, or
      (ii) a tension force sensor coupled with the movable member or the anvil, wherein the tension force sensor is configured to sense a tension force communicated longitudinally through the movable member during at least one of compressing the tissue between the anvil and the deck surface or firing the surgical instrument.

2. The surgical instrument of claim 1, wherein the force sensing assembly comprises the compression force sensor disposed between the first and second housings.

3. The surgical instrument of claim 2, wherein the compression force sensor includes a load cell.

4. The surgical instrument of claim 2, wherein the first housing includes a body member configured to surround at least a portion of the movable member, wherein the second housing includes a deck member, wherein the deck member includes the deck surface, wherein the compression force sensor is configured to sense the compression force between the body member and the deck member during compressing the tissue between the anvil and the deck surface.

5. The surgical instrument of claim 4, wherein the compression force sensor includes an annular ring that surrounds at least a portion of the deck member during compressing the tissue between the anvil and the deck surface.

6. The surgical instrument of claim 2, wherein the first housing includes an outer sheath configured to surround at least a portion of the movable member, wherein the second housing includes a body member configured to surround at least a portion of the movable member, wherein the outer sheath is fixed relative to the body member, wherein the compression force sensor is configured to sense the compression force between the outer sheath and the body member during compressing the tissue between the anvil and the deck surface.

7. The surgical instrument of claim 2, wherein the first housing includes a handle assembly configured to be gripped by a user, wherein the second housing includes an outer sheath configured to surround at least a portion of the movable member, wherein the handle assembly is fixed relative to the outer sheath, wherein the compression force sensor is configured to sense the compression force between the handle assembly and the outer sheath during compressing the tissue between the anvil and the deck surface.

8. The surgical instrument of claim 2, wherein the first housing includes an actuator configured to translate the movable member, wherein the second housing includes a handle assembly configured to be gripped by a user, wherein the compression force sensor is configured to sense the compression force between the actuator and the handle assembly during at least one of compressing the tissue between the anvil and the deck surface or the firing the surgical instrument.

9. The surgical instrument of claim 1, wherein the anvil includes a head and a shaft, wherein the shaft is configured to be selectively coupled with the movable member to compress tissue between the anvil and the deck surface, wherein the tension force sensor is coupled with the movable member or the shaft of the anvil.

10. The surgical instrument of claim 9, wherein the movable member includes a trocar actuation connecting assembly, wherein the tension force sensor is fixably coupled with the trocar actuation connecting assembly.

11. The surgical instrument of claim 10, wherein the trocar actuation connecting assembly includes upper and lower tension bands, wherein the tension force sensor is fixably coupled with the upper tension band.

12. The surgical instrument of claim 9, wherein the tension force sensor includes an in-line strain gage.

13. The surgical instrument of claim 9, wherein the movable member includes a trocar actuation band assembly and a trocar, wherein the trocar is translatably coupled with the trocar actuation band assembly, wherein the tension force sensor is disposed on the trocar actuation band assembly, the trocar, or between the trocar actuation band assembly and the trocar.

14. The surgical instrument of claim 1, further comprising a control system, wherein the force sensing assembly includes a wire that electrically connects at least one of the tension force sensor or the compression force sensor with the control system.

15. The surgical instrument of claim 14, wherein the control system includes a user display feature, wherein the control system is electrically coupled with the user display feature, wherein the user display feature is configured to at least one of display the compression or tension force, display whether the compression or tension force is within an acceptable range, record the compression or tension force, or the upload the compression or tension force to a cloud.

16. A surgical instrument comprising:
(a) a handle assembly, wherein the handle assembly includes a casing;
(b) a shaft assembly extending distally from the handle assembly, wherein the shaft assembly includes an outer sheath, a trocar actuation rod, and a trocar actuation connecting assembly;
(c) a stapling head assembly extending distally from the shaft assembly, wherein the stapling head assembly comprises:
(i) a body member,
(ii) a deck member that includes an annular array of staple openings, and
(iii) a trocar;
(d) an anvil that includes a head and a shaft, wherein the shaft is configured to be selectively coupled with the trocar to compress tissue;
(e) an actuator that is configured to translate the trocar relative to the handle assembly; and
(f) a force sensing assembly, wherein the force sensing assembly comprises:
(i) a compression force sensor configured to sense compression force communicated longitudinally through the surgical instrument, wherein the compression force sensor is positioned between:
(1) the deck member and the body member,
(2) the body member and the outer sheath,
(3) the outer sheath and the casing, or
(4) the casing and the actuator, or
(ii) a tension force sensor coupled with at least one of the trocar actuation rod, the trocar actuation connecting assembly, the trocar, or the shaft of the anvil, wherein the tension force sensor is configured to sense tension force communicated longitudinally through the shaft assembly, the trocar, or the anvil.

17. A method of using a surgical instrument, the surgical instrument comprising a housing assembly comprising first and second housings that are disposed adjacent one another, and a deck surface that includes at least one annular array of staple openings, a movable member at least partially disposed within the housing assembly, an anvil configured to be selectively coupled with the movable member, and at least one of a compression force sensor or a tension force sensor, the method comprising:
(a) compressing tissue between the anvil and the deck surface;
(b) firing the surgical instrument to drive staples through the tissue;
(c) measuring at least one of:
(i) a compression force communicated longitudinally between the first and second housings while at least one of compressing tissue between the anvil and the deck surface or firing the surgical instrument, using a compression force sensor disposed between the first and second housings, or
(ii) a tension force communicated longitudinally through the movable member while at least one of compressing the tissue between the anvil and the deck surface or firing the surgical instrument, using a tension force sensor coupled with the movable member; and
(d) based on at least one of the compression force or the tension force, determining at least one of:
(i) a force with which the surgical instrument compresses tissue disposed between the deck surface and the anvil at a time prior to firing of the surgical instrument, or
(ii) a force with which a firing assembly of the surgical instrument is actuated to fire the surgical instrument on the compressed tissue.

18. The method of claim 17, further comprising, after determining the tissue compression, producing an indication that tissue compression is within an acceptable range.

19. The method of claim 17, wherein the step of measuring further comprises correlating the measurement of the compression force or the tension force to an amount of tissue compression prior to firing of the surgical instrument or during firing of the surgical instrument using an algorithm.

20. The method of claim 17, further comprising, after determining at least one of forces, uploading at least one of the forces to a cloud.

* * * * *